(12) United States Patent
Saeed

(10) Patent No.: US 8,118,862 B2
(45) Date of Patent: Feb. 21, 2012

(54) APPARATUS AND METHOD FOR IMPLANTATION OF BIFURCATED ENDOVASCULAR PROSTHESIS

(76) Inventor: Mohsin Saeed, La Jolla, CA (US)

( * ) Notice: Subject to any disclaimer, the term of this patent is extended or adjusted under 35 U.S.C. 154(b) by 66 days.

(21) Appl. No.: 12/157,736

(22) Filed: Jun. 12, 2008

(65) Prior Publication Data

US 2008/0255656 A1    Oct. 16, 2008

Related U.S. Application Data

(63) Continuation-in-part of application No. 12/072,073, filed on Feb. 21, 2008, now abandoned, which is a continuation-in-part of application No. 11/888,031, filed on Jul. 30, 2007.

(60) Provisional application No. 60/903,253, filed on Feb. 22, 2007.

(51) Int. Cl.
*A61F 2/06* (2006.01)

(52) U.S. Cl. ...................... 623/1.35; 623/1.11; 623/1.13; 623/1.23

(58) Field of Classification Search ............... 623/1.13, 623/1.23, 1.35; 606/108, 113, 198
See application file for complete search history.

(56) References Cited

U.S. PATENT DOCUMENTS

| 6,517,550 B1 * | 2/2003 | Konya et al. | 606/113 |
| 2005/0182476 A1 * | 8/2005 | Hartley et al. | 623/1.11 |

* cited by examiner

*Primary Examiner* — Todd E Manahan
*Assistant Examiner* — Kevin Everage
(74) *Attorney, Agent, or Firm* — Donn K. Harms

(57) ABSTRACT

A stent graft for animal or human implantation and method of delivery thereof. The device stent graft employs a first component having an axial passage communicating with the axial cavities of a cuff and longer first leg. A separate leg extension is engageable to an aperture in the distal end of the cuff. A first catheter engages the first component for translation to the implantation site along a first guide wire. A guide member communicating through the first component and extending from the distal end of a second catheter and adapted for slidable contact along the first guide wire when pushed by a translatable core shaft extending from the first catheter, or by the second catheter, is provided as a pre-positioned guide for subsequent engagement of the leg extension to the aperture in the distal end of the cuff. Translation of the core shaft while in contact with the guide member pulls a third guide engaged with the second catheter into the cuff to provide a track for proper and speedy positioning and engagement of the leg extension with the cuff.

16 Claims, 14 Drawing Sheets

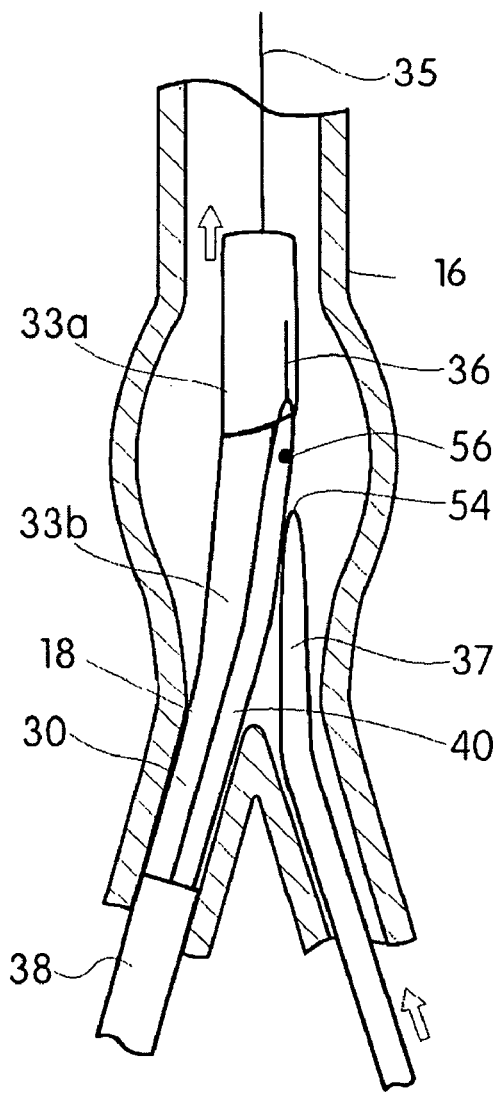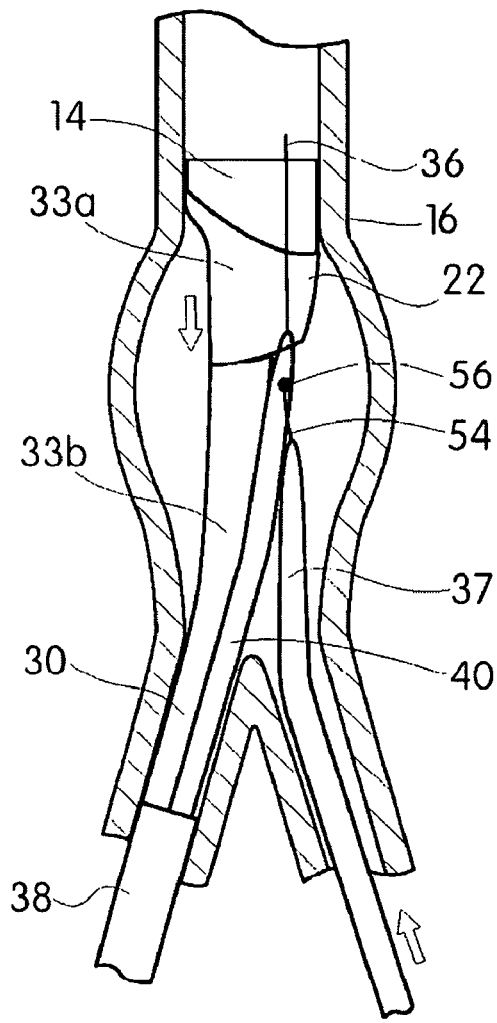
Fig. 5
Fig. 6

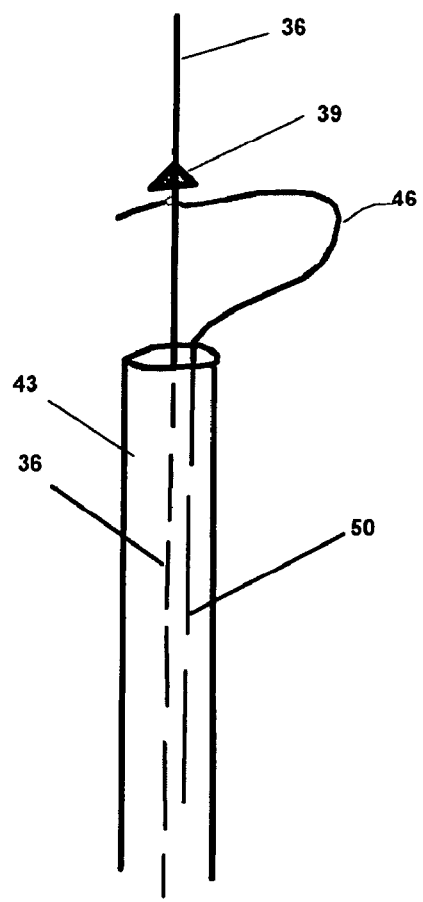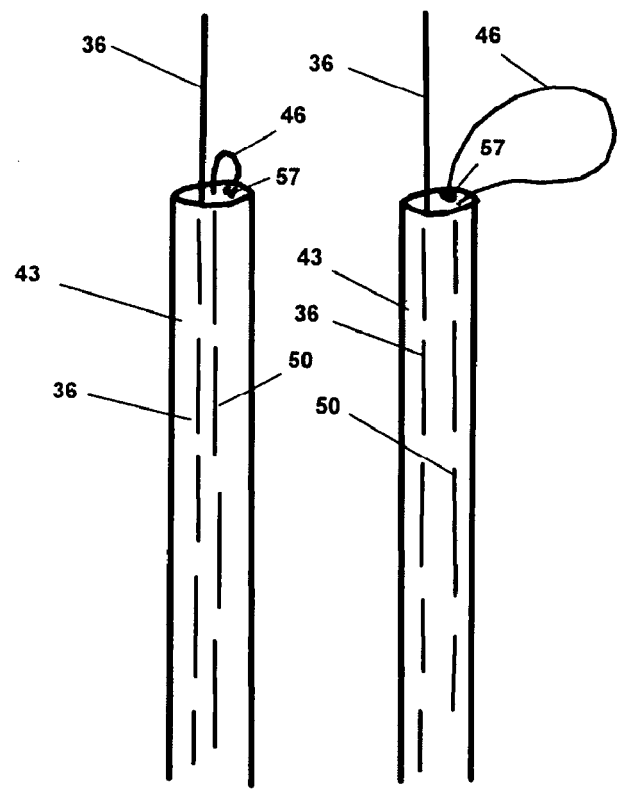
Fig. 14  Fig. 15a  Fig. 15b

APPARATUS AND METHOD FOR IMPLANTATION OF BIFURCATED ENDOVASCULAR PROSTHESIS

This application is a Continuation in Part of U.S. patent application Ser. No. 12/072,073 filed Feb. 21, 2008 now abandoned, and which is incorporated herein in its entirety by reference, which is a Continuation in Part of U.S. patent application Ser. No. 11/888,031, filed Jul. 30, 2007, and which is incorporated herein in its entirety by reference, which claims priority from U.S. Provisional Patent Application Ser. No. 60/903,253 filed Feb. 22, 2007, also incorporated herein in its entirety by reference.

FIELD OF THE INVENTION

The disclosed device relates to an endovascular prosthesis and implantation method therefor. More particularly it relates to a device and method for implantation of a bifurcated endoprosthesis for repair of infrarenal abdominal aortic aneurysms commonly known to those skilled in the art as AAA's.

BACKGROUND OF THE INVENTION

An aneurysm is a type of disease that affects the arteries and is manifested by a localized widening or enlargement of an artery compared to its normal size. Because of the potential of rupture of the artery in question, any aneurysm is a serious health problem and risk to a patient. When a blood vessel with an aneurysm ruptures, life-threatening bleeding generally is the result. Even prior to such an occurrence, aneurysms can also cause pain from pressure on nearby organs or nerves, and on occasion, debris within the aneurysm can dislodge and thereafter be communicated through the circulatory system of the patient to the legs or vital organs. The result is generally a blocking of the blood flow to these tissues and resulting harm to organs and tissues remote to the aneurysm itself.

A common location for aneurysms is in the abdominal aorta, which is one of the largest blood vessels in the body and located in the abdominal region of the body. A rupture of such a large blood vessel has dire and life threatening consequences to the individual suffering such a crisis. Such abdominal aortic aneurysms (AAAs) most often involve the infrarenal aorta which is the portion of the blood vessel that lies below the takeoff of the arteries to the kidneys (renal arteries). About half of AAAs also involve the iliac arteries in the pelvis. The major risk associated with AAAs is that they have a high propensity to rupture, and currently such ruptures are the 13th leading cause of death in the United States. Therefore, early detection and timely repair are paramount to the patient.

Current medical practice which is least invasive to the patient employs endovascular repair or stent grafting in a procedure which is performed through small incisions in each groin. While carrying many of the same risks as invasive surgical repair, patients usually spend fewer days in the hospital and recover more quickly with less pain with the implantation of an endovascular prosthesis.

In a procedure to implant the prosthesis, a bifurcated stent graft is positioned within the aneurysm to provide a new conduit for blood flow through the damaged portion of the blood vessel. This effectively seals off the diseased and bulging portion of the aorta from the blood flow and eliminates the potential for rupture.

A common endoprosthesis for repair of an AAA is a two-piece bifurcated endovascular graft which is positioned to line the aorta within the aneurysm and has a first portion adapted to engage within the aorta, which communicates with two graft conduits, and which extends from below the renal arteries into both iliac arteries. Material such as ePTFE (expanded polytetrafluoroethylene) forming this fluid conduit for blood flow is commonly inert when implanted. A structural metallic component known generally as a stent is engaged in a skeletal arrangement with the material to maintain the formed conduits for blood flow in an expanded condition once implanted.

Delivery and implantation of the device to the site of the aneurysm in the abdominal aorta is generally done by assembly of two component sections which include the trunk with a cuff adapted to engage the contralateral leg. The trunk portion has a large diameter adapted to engage within the large internal diameter of the aorta and is implanted to a position just below the renal arteries. Extending from the trunk and having an internal conduit in communication with the internal passage of the trunk portion is the ipsilateral leg which is positioned in communication within one of the iliac arteries when deployed. The trunk and first leg are conventionally formed and deployed as a unitary structure. The cuff also extends from the trunk portion and, as noted, is adapted for engagement to the second leg which is positioned once engaged within a second of the iliac arteries. The engagement of the contralateral leg with the cuff and positioning of its distal end within the other of the iliac arteries completes the stent graft.

This two-piece construction is required because of the nature of the engagement of the two legs from the trunk into two different iliac arteries. However, assembly of these two components inside the body of the patient during surgery can be a vexing task to even the most experienced and knowledgeable surgeon. This is because the visual display depicting the components during assembly is a two-dimensional video visualization of a three-dimensional communication between the components of the implant and the two iliac arteries in their junction to the aorta. These arteries generally engage with the aorta at angles radial to the axis of the aorta which must be accommodated during the engagement of the contralateral leg portion with the short extending cuff from the trunk portion.

Currently, the trunk portion and first leg portion are advanced using a catheter and guide wire through an incision in one of the femoral arteries. Once inserted into a femoral artery, the trunk and extending first leg and cuff are advanced over the guide wire to the proper position at the juncture of the aorta and renal arteries. During this translation into the aneurysm, the trunk, cuff, and ipsilateral leg are held in a compressed state at the distal end of the catheter by a restraining mechanism which can at a chosen time be released by controls positioned outside the patient's body to allow the stent graft to enlarge to its expanded state, thereby engaging within the vessel at the appropriate point. Once proper positioning is determined by the surgeon using radiopaque markers and fluoroscopic visualization of the distal end of the first catheter, a control mechanism communicating with the restraining mechanism is activated. This allows for enlargement of the trunk and first leg in their respective positions in the aorta and iliac artery.

It is at this point in the procedure that the surgery can become uncertain as to duration and an ongoing source of frustration to the surgeon. Attachment of the second or contralateral leg to the distal end of the cuff portion extending from the trunk is achieved by translating a guide wire from the second leg artery which must be visually guided into the aperture at the distal end of the cuff extending from the trunk. Once so positioned, the contralateral leg may be translated over the guide wire and into proper position relative to the cuff and enlarged to engage the contralateral leg to the cuff.

While this may sound like a simple procedure in principle, in practice it is both frustrating and can be extremely time consuming. The extra time in the operating room and uncertainty as to operation duration impacts the surgery schedules for subsequent surgeries. Additionally, during this engagement process of the contralateral leg to the cuff, the patient remains under anesthesia, exposed to continual x-ray radiation, and subjected to continued manipulation of the guide wire inside the vessel adjacent to the cuff. Since there is usually extensive clot and atherosclerotic plaque within the aneurysm, such manipulation entails the additional risk of dislodging debris within the lumen of the aneurysm, thereby also raising the risk of such debris traveling to branch arteries of the aorta.

The primary problem in this engagement step arises from the wide variance of intersecting angles of the radially extending iliac arteries from the aorta. The resulting angles of the graft legs may be highly divergent from the axis of the trunk. However, in the two-dimensional visualization provided by the fluoroscope, the surgeon is visually hindered in the attempt to thread the guide wire into the aperture at the distal end of the cuff. An additional factor complicating wire passage into the cuff is that the cuff is usually near the center of the large cavity formed by the aneurysm which in many cases can exceed 10 cm in diameter. The engagement of a small diameter cuff positioned in the midst of such a comparatively large space with the aid of only two-dimensional imaging, while concurrently contending with the highly variable angles of approach from the iliac arteries, renders the procedure very unpredictable.

Further, in many cases the angles leading to the iliac arteries from the aorta are such that the surgeon will choose to cross over the first leg and contralateral leg in an overlapping arrangement to maintain a continuous curve for blood flow and to avoid kinks. When graft legs are crossed, attempts at passage of a wire from the second iliac artery into the cuff may additionally be complicated by interference from the first leg which, when positioned in the cross-leg deployment format, will lie across the opening from the second iliac artery into the aorta. Even highly trained surgeons with years of experience can become bogged down trying to thread the guide wire into the aperture of the cuff using the two dimensional visualization and overlapping of images available on the fluoroscopic screen. Absent a lucky positioning of the guide wire, such an exercise can consume an inordinate amount of time.

As such, there exists an unmet need for a bifurcated endoprosthesis which can be more easily assembled from components to repair aortic aneurysms. Such a device should allow for conventional deployment of the trunk portion and first extending leg and cuff in a relatively conventional fashion to facilitate easy adoption of the device and procedure. However, such a device and method should provide a means to eliminate the frustration and time-consuming step requiring the surgeon to fish with the distal end of a second guide wire for the aperture of the cuff extending from the trunk portion. In this fashion, implantation surgeries for such devices may be expedited and performed with a reasonably accurate estimate of duration, and patients undergoing such surgeries will benefit from shortened procedures and be spared exposure to prolonged radiation.

In this respect, before explaining at least one embodiment of the invention in detail, it is to be understood that the invention is not limited in its application to the details of construction and to the arrangement of the components set forth in the following description or illustrated in the drawings nor the steps outlined in the specification. The invention is capable of other embodiments and of being practiced and carried out in various ways as those skilled in the art will readily ascertain from reading this application. Also, it is to be understood that the phraseology and terminology employed herein are for the purpose of description and should not be regarded as limiting.

As such, those skilled in the art will appreciate that the conception upon which this disclosure is based may readily be utilized as a basis for designing other methods and systems for carrying out the several purposes of the present invention of a device and method for implanting a bifurcated prosthesis in an aortic aneurysm. It is important, therefore, that the claims be regarded as including such equivalent construction insofar as they do not depart from the spirit and scope of the present invention.

OBJECTS OF THE INVENTION

An object of this invention is the provision of a bifurcated prosthesis for repair of aortic aneurysms.

An additional object of this invention is the provision of such a prosthesis which may be assembled from multiple components with ease and in a much reduced duration from a conventionally available device.

Yet another object of this invention is to provide a plurality of means to restrain the implantable prosthesis in a compressed state such that controlled release of the restraining mechanism employed is achievable. The restraint system allows for incorporation of a novel component adapted for capture of an additional guide wire into the overall apparatus in a manner optimizing function of the device.

Yet another object of this invention is the provision of a method of implantation of such a device which pre-positions a guide wire or member within a cuff or aperture of the device to guide a second leg to the trunk portion of the device and into proper engagement, thereby eliminating the time-consuming task of fishing for the cuff aperture.

Another object of this invention is to provide a method of capturing a secondary guide wire during assembly of a bifurcated stent graft procedure and guiding it into a targeted aperture using a snare or other capture means which may be engaged to a catheter which will slide on the pre-positioned guide wire.

Yet another object of this invention is to provide a device and method of secondary guide wire capture and guide to a target aperture by provision of a catheter and snare combination and pre-positioned second, or escort, catheter.

A yet additional object of this invention is to provide a method of capturing a secondary guide wire used for the assembly of a bifurcated stent graft procedure, which allows for capture of the secondary guide wire, before the body of the graft is implanted, instead of afterwards thereby alleviating concerns about this previously tricky and tedious step.

These together with other objects and advantages which will become subsequently apparent reside in the details of the construction and operation as more fully hereinafter described and claimed, reference being had to the accompanying drawings forming a part thereof, wherein like numerals refer to like parts throughout.

SUMMARY OF THE INVENTION

The device and method herein feature a modular bifurcated vascular prosthesis which is assembled in the artery of a patient from a plurality of components adapted for mutual engagement and placement within a diseased aorta to provide a new conduit for blood flow therethrough.

As currently practiced, attempts to engage the contralateral cuff portion of the graft with a guide wire commence after the graft is deployed. As previously mentioned, this is encumbered by several factors, notably the small size of the target within a large aneurysm cavity, variably complex angles of approach imposed by iliac artery orientation relative to the axis of the aorta, and possible interference from the deployed long leg of the graft when a crossed-leg deployment is chosen.

The device and method disclosed herein obviates these difficulties through employment of several novel strategies and structures. Firstly, the time-consuming and unpredictable requirement of current art to maneuver a direct wire passage from the second iliac artery into the cuff after deployment of the device is eliminated. Instead, a maneuver is substituted which provides for easy capture of a guide wire from a catheter introduced from a second iliac artery, before or after implantation of the main body of the graft, by provision of means for capture of its distal end in a positive mechanical engagement.

Because of the manipulation of the device and captured guide wire subsequent to capture, it is especially important that the capture be secure until the surgeon decides to release that capture. This capture device in a current preferred mode employs a snare. The snaring function is enabled by a novel device which is a key component of the overall apparatus. The device, also referred to as the "escort catheter" in the text, is a narrow diameter, semi-rigid catheter having a central coaxial lumen allowing for passage of a second guide wire therethrough over which the catheter can be translated, and which second guide wire can be pre-positioned inside the cuff portion extending from the main trunk of the stent graft.

Also incorporated into the escort catheter is an eccentric lumen the proximal end of which lumen is accessed through a locking, rotatable valve attached externally near the back end of the escort catheter. The distal end of the eccentric lumen communicates with an aperture in the wall of the escort catheter some distance from the distal tip of the escort catheter. A snare wire passes through the locking valve, runs within the eccentric lumen, and has its tip tethered to the catheter wall at the aperture. Forward translation of this wire extrudes a desired length of wire from the aperture, the extruded length assuming the shape of a snare loop, projecting orthogonally to the axis of the catheter. Loop formation and its orthogonal projection are aided by incorporation of pre-shaped memory into the wire.

The snare loop can be closed by retraction of the wire and held securely in the closed position by locking the rotating valve around the wire. The escort catheter depicted in FIG. 2, and FIG. 2a illustrates the incorporation of this catheter into the shaft of the main delivery catheter, the function of this integrated unit being detailed elsewhere in the text. Extending from this escort catheter is the second guide wire which is pre-positioned inside the cuff of the graft during assembly. This second guide wire thereby provides a pre-positioned guide for translation of a captured third guide wire directly into the cuff portion of the device.

Additional utility and benefit to the patient is provided by the fact that this capturing maneuver is transferred to a location within the vascular system far more favorable than the center of a large aneurysm cavity. Specifically, capture of the third wire from a second catheter is executed at the confluence of the two iliac arteries as they converge at the bottom of the aneurysm. The second catheter with the third guide wire introduced from the second iliac artery is predictably engaged by the snare loop of desired dimension and shape which projects across the opening of the iliac artery. This arrangement exploits the inevitable convergence of the second catheter and its guide wire and the snare-bearing device engaged with the delivery catheter from the first iliac artery.

Further utility in the disclosed device is provided through the incorporation of the positioning or escort catheter in a translatable communication through the graft-bearing delivery catheter or sheath. Such a collinear engagement provides the surgeon freedom of orientation of the snare loop at the opening of the second iliac artery by translation and rotation of the catheter assembly to optimally position the snare for capture of the second guide wire.

Still further, after capture of the third guide wire extending from the second catheter, the entire engaged apparatus can be translated and rotated at will, thereby enabling the surgeon to provide precise graft positioning as well as rotational orientation for crossing the legs of the device to whatever degree is dictated by patient anatomy. Such maneuvers can be executed without risk of loss of the captured third guide wire because of the security conferred by design of the snare and an engagement bead positioned at the distal end of the third guide wire extending from the secondary catheter. This mechanical engagement insures that the capture will remain intact until the surgeon initiates a manual release.

In this particularly preferred mode of the disclosed device and method, a bead is engaged upon the extended third guide wire of the secondary catheter. To allow easy withdrawal of the third guide wire through the secondary catheter, the proximal profile of the bead needs to be tapered so as to align with the lumen easily. This attribute would, however, be in conflict with the requirement that the bead be securely captured in the snare loop which would be aided by the bead having an abrupt proximal profile.

Therefore, the third guide wire from the secondary catheter in one preferred embodiment employs an abruptly fashioned bead which may not be removable through the lumen of the secondary catheter from which it translates. Using this mode of the device would therefore require that a wire exchange be executed by the surgeon using conventional wide lumen sheaths to position a heavy-duty angiographic wire inside the cuff over which the contralateral leg may be translated into the cuff.

Of course those skilled in the art will no doubt realize that the device may be employed to take advantage of the pre-positioned escort catheter guide wire in the cuff of the contralateral leg in combination with the operation of a snare or other means of capture to secure and guide some type of guide wire from the secondary catheter to be employed as a means to guide the contralateral leg into engagement with the cuff. Further, the method of positioning a capture device adjacent to the distal end of the main delivery catheter and pre-positioning a guide wire in the cuff of the contralateral leg may be employed with currently manufactured devices. The employment of this method with all such devices is anticipated as included herein.

Still further, while a two-step expansion system is described herein for the trunk and leg portions of the device, it is anticipated that a one-step expansion could be employed in a less preferred method and mode of the device which would require extraction of the second catheter from a position sandwiched between the engaged first leg and the iliac artery, and such is anticipated.

Finally, by employing a means to capture the secondary guide wire projecting from or engaged to the escort catheter, the steps in the implantation procedure can be altered to allow the surgeon to capture the secondary guide wire before expanding the main body of the implant. The subsequent guiding of the contralateral leg into place is therefore assured before implantation of the main body saving time and easing concerns about this conventionally time-consuming step in the procedure.

The device herein disclosed, as noted, has a first component which includes a trunk portion with an enlarged diameter adapted to engage within the walls of the aorta. In addition to the trunk portion, the first component has two smaller conduits extending from a lower end of the trunk opposite the open aperture of the trunk portion. An ipsilateral or first leg has a diameter and a length adapted to allow it to extend into an engaged position communicating between the trunk and one of the iliac arteries when the first component portion is deployed to its enlarged position. The other shorter conduit is a cuff portion which also extends from the lower end of the trunk portion. The shorter cuff portion has an aperture at a distal end. The distal end of the cuff is adapted for engagement to an engagement end of the second or contralateral leg which is the second component of the assembled device.

The trunk, first leg, and cuff forming the first component are adapted to be collapsed to a compressed position and held in that state by a removable sheath or other means of releasable restraint of the first component when engaged at the distal end of a first delivery catheter. A release mechanism is engaged within or along the first delivery catheter to allow a sequential release of the restraining mechanism at a desired time in the procedure. In a preferred mode of the device herein disclosed, the releasable restraint would provide two separately releasable component portions that would allow for expansion of the trunk and cuff portions of the device in a first step and the remainder of the device subsequent to engagement of a third guide wire into the cuff portion.

A second component of the device is a second leg portion which is engaged to a second delivery catheter in a collapsed state for translatable delivery along the properly positioned secondary guide wire to an engagement with the expanded cuff of the first component. As noted, the engagement end of the contralateral or second leg is adapted to cooperatively engage with the distal end of the expanded cuff to thereby yield a second conduit for blood flow from the trunk portion and into the second of the two iliac arteries once the device is fully assembled and deployed.

A projecting first guide wire is positioned in the body to provide a guide to the first delivery catheter which is advanced thereover to place the graft-bearing portion or distal end of a first delivery catheter in a proper positioning. The trunk and first leg are held by a fabric sheath or other restraining mechanism in a collapsed position. An escort catheter is slidably engaged within the first delivery catheter and has a projecting end portion which extends from an exit aperture in the first delivery catheter. This end portion is substantially exposed except for a tip portion which is held under the restraint.

A second guide wire extending from the distal end of the escort catheter is pre-positioned within the cuff portion extending from the trunk of the first component prior to compression to the collapsed state. Once in the collapsed state, this second guide wire extending from the projecting end portion of the escort catheter thereby remains pre-positioned in the cuff.

As noted, also incorporated into the escort catheter of the device is a snare which is preferably formed of memory material such as nitinol. This snare is extendable from an exit aperture communicating through the sidewall of an uncovered portion of the escort catheter. A snare control wire for cinching the projecting snare is translatably engaged axially through the escort catheter to a rotating valve positioned exterior to the body of the patient. The cinch can thus be extended to an enlarged loop, or collapsed, by translation of the control wire. Using memory material, the enlarged loop may be preformed with a memorized shape and projection, such that the loop so projected is orthogonal to the axis of the escort catheter and is of a size best adapted to the task of capturing a third guide wire extending forward from the secondary catheter which is also operatively engaged to this guide wire.

In the method of implantation, the first component formed of the trunk, first leg, and cuff in the above-noted collapsed position on the end of the first delivery catheter is translated over a pre-positioned first guide wire through a femoral artery to thereby position the trunk within the aorta at the site of the aneurysm. To this end, the first delivery catheter is extended up through one of the iliac arteries to position the trunk portion in the aorta and concurrently place the first leg within that iliac artery.

Prior to activation of the mechanism which releases a first portion of the employed means for restraining the upper half of the first component in the collapsed position, the snare is extended from the uncovered portion of the escort catheter to form a loop by translating the snare wire. The loop, as noted, is positioned at the juncture of the second iliac artery and the aorta by extension of the snare and/or translation of the escort catheter. Once positioning of the first component and the snare is properly confirmed using the fluoroscope or other means, the second catheter is translated up the opposite leg artery toward the first component. The third guide wire extending from the distal end of the secondary catheter has a bead or small terminating component fixed to its distal end to provide a grip for the snare.

During this step, the distal end of the third guide wire extending from the second catheter is translated to a point wherein it traverses through the extended loop of the projecting snare which is positioned around the iliac artery juncture with the aorta. Once traverse of the second guide wire through the loop of the snare is confirmed, the snare control wire is translated to cinch the loop of the snare and capture the distal end of the third guide wire extending from the second catheter. A locking rotatable valve is then set to hold the snare in the closed position.

At this juncture in the method of deployment the disclosed device with the captured third guide wire may be manipulated into proper position relative to the aorta and iliac arteries by the surgeon to provide a precise graft positioning depending on the surgeon's chosen mode of leg and trunk orientation of the device within the patient. As noted, this maneuver can be accomplished without risk of loss of the captured second guide wire since it is secure in the snare and only subject to release by the positive action of the surgeon to do so. Once properly positioned by the surgeon, the first portion of the compressed first component may be fully deployed from the compressed state to the enlarged state, thereby seating the trunk in the aorta and the cuff in expanded mode. The first or longer engaged leg remains compressed for subsequent deployment in the chosen one of the two iliac arteries.

Once the first component is so expanded, the novelty and utility of the disclosed device become evident. Since the third guide wire of the secondary catheter is already captured by the snare and the second guide wire extending from the escort catheter is pre-positioned within the now expanded cuff, it is a short and simple process to translate the escort catheter, along with the snare-engaged guide wire of the secondary catheter, along the second guide wire into the cuff and subsequently translate the secondary catheter, or subsequent devices, over the third guide wire and into the cuff.

As noted earlier, with the third guide wire extending from the secondary catheter positioned in the cuff, any of a number of conventional wire exchanges may be executed by the surgeon using this third guide wire from the secondary catheter to place a conventional heavy duty guide wire into the cuff, over which the catheter bearing the contralateral leg may be advanced for engagement into the cuff.

As an example, the surgeon may advance a wide lumen sheath over the third guide wire to thereby position its distal end inside the cuff. Thereafter, the third guide wire may be removed through the wide lumen axial cavity of the sheath and a guide wire of the surgeon's choice may be properly positioned through the axial cavity to place its distal end inside the cuff. Using this subsequently placed wire, the surgeon would then advance a secondary delivery catheter bearing the second leg thereover to properly position the contralateral or second leg within the distal end of the cuff. The contralateral leg is then deployed by activating a control to release the constraining mechanism holding it in a collapsed state, as is the first leg in the secondary employment of the first component of the assembled device. Once so deployed, the engagement end of the properly positioned contralateral leg enlarges to a fixed engagement with the cuff, thereby providing the second sealed conduit between the aorta-engaged trunk and the second iliac artery. This completes assembly of this device.

As those skilled in the art will realize, other means to releasably engage the secondary catheter guide wire to the escort catheter, or its equivalent, extending exposed from the first delivery catheter, or a conventional sheath type delivery component such as those manufactured by the Cook Group of Bloomington, Ind., might be employed. Consequently, any such means for capturing a secondary guide component which may then translate along a pre-positioned wire or other guide means into an aperture of an assembleable implant such as a stent graft, to thereby position the secondary guide component within the aperture of the implant to be assembled and to allow the secondary guide component to subsequently guide part of the stent graft being assembled to an engagement with the aperture, as would occur to those skilled in the art, is anticipated.

Because of the confined working environment, the compactness and ease of operation of the snare, the ability to provide memorized shapes to the snare formed of memory material, the ability to provide varying angles during deployment, and the resulting positive releasable mechanical engagement of a cinched snare to a secondary guide component used to guide subsequent placement of the contralateral leg or similar component, the current preferred mode of the device preferably employs a snare to capture the secondary guide component. Once so captured, the secondary guide component may be translated into the aperture or cuff along the pre-positioned wire or guide, and thereafter provide the subsequent path for the contralateral leg with its engagement to the cuff. Employing a capture component that itself is engaged to travel along a pre-positioned wire or guide into the cuff thereby provides a much faster, safer, and more efficient manner to assemble an implant of multiple components within the patient from that the current art.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing summary and following detailed description are considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

BRIEF DESCRIPTION OF THE DRAWINGS

FIG. 5 depicts translation of the device into the aorta subsequent to capture of the second lead wire.

FIG. 6 shows initial deployment, by release of a first portion of the two stage restraint through a release of the constraining stitch allowing expansion of the trunk portion of the device in the aorta.

FIG. 14 depicts another mode of the device herein showing the snare-type capture component projecting from the distal end of the same lumen or sheath housing the second guide wire and engaged to the guide wire.

FIGS. 15a and 15b depict the deployment and constriction of the snare type capture device by translation of one or both of the sheath and control wire.

DETAILED DESCRIPTION OF THE INVENTION

Figure 1:
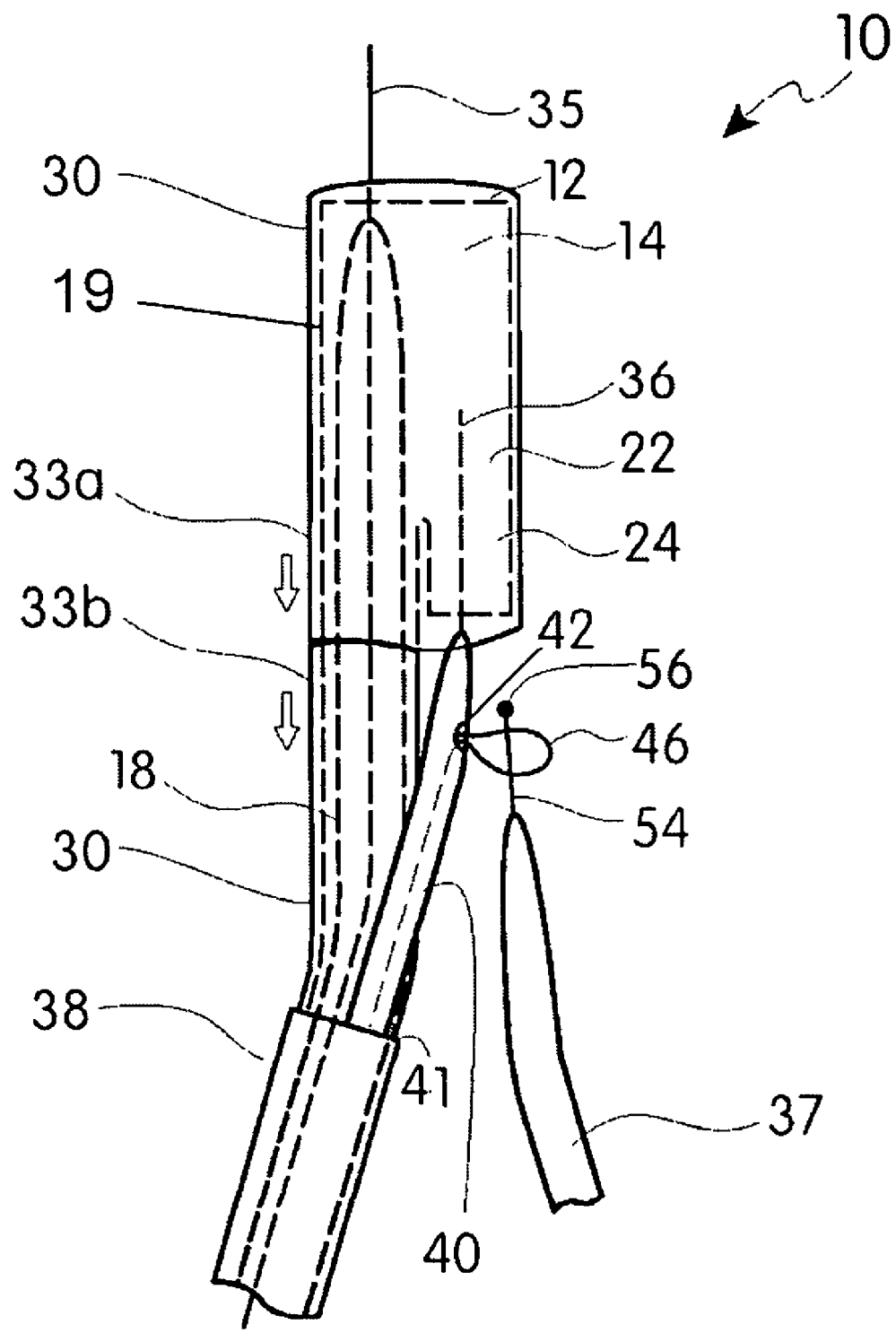
FIG. 1 is a depiction of the device showing a delivery catheter having a snare capture component extending from an exposed aperture in an escort catheter.
Figure 9:
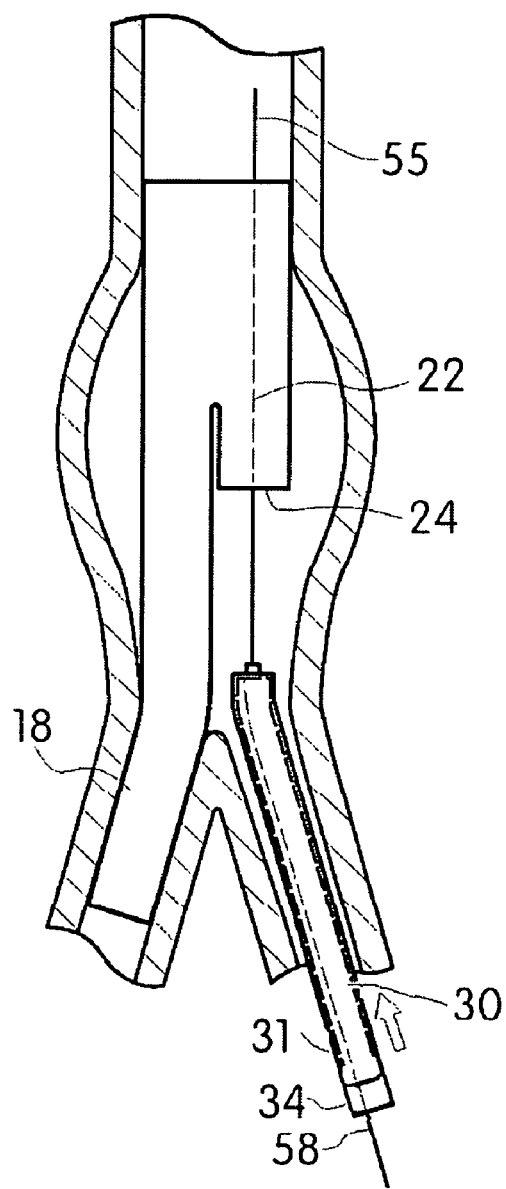
FIG. 9 depicts a subsequent guide wire located in the cuff after the surgeon executes a wire exchange with the second lead wire and a subsequent advancement of the restrained second leg along the chosen guide wire for engagement in the cuff.
Figure 10:
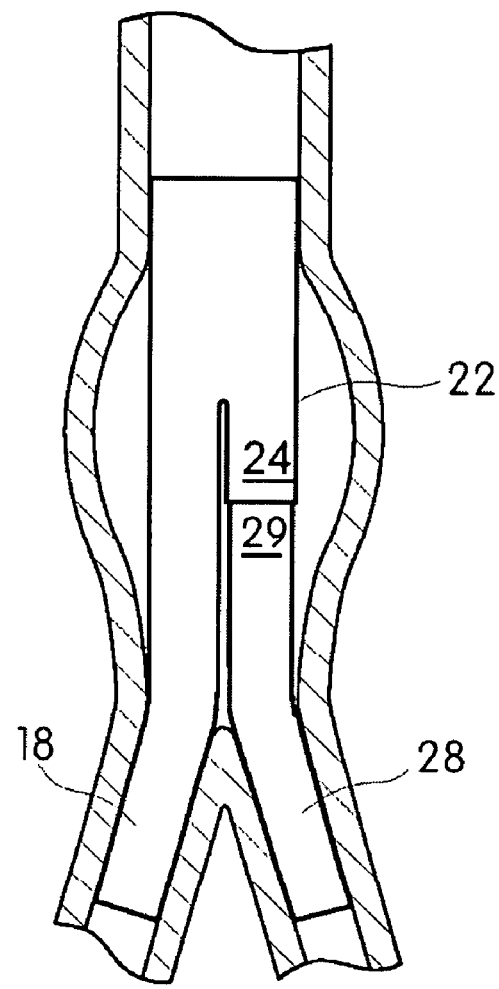
FIG. 10 shows the second leg of the device in an expanded engagement with the cuff subsequent to release of restraint mechanism holding the second leg collapsed.

Referring now to the drawings in FIGS. 1-20, wherein similar parts are identified by like reference numerals, the device 10 is depicted in FIG. 1 which illustrates the components of a conventional bifurcating prosthesis 12 engaged to the distal end of a delivery catheter 38. A trunk portion 14 is shown having a diameter adapted to engage within the walls of the aorta 16 shown in FIGS. 4-6. The trunk portion 14 is in communication with two smaller conduits extending from a lower end of the trunk 14, communicating with the larger open aperture at the upper end of the trunk 14. An ipsilateral or first leg 18 shown in FIG. 1 and FIGS. 4-10, has a diameter and a length adapted to extend into an engaged position communicating between the trunk 14 and one of the iliac arteries. The other shorter conduit shown in FIGS. 1 and 2a, is a cuff 22 portion extending from the lower end of the trunk 14 portion. As shown in other figures such as FIG. 10, the distal end 24 of the cuff 22 is adapted for engagement to one end of the contralateral or second leg 28 of the assembled device 10 as depicted in FIG. 10.

In use adapted for deployment, the trunk 14, first leg 18, and cuff 22 forming the first component are initially in a collapsed position and held in that state by means of a releasable restraint adapted to the task, which is shown in FIG. 1 as a fabric sheath 30 having a release stitch 31 as a release mechanism to deploy the restraint as best shown in FIG. 2a. The release stitch 31 shown in FIG. 2a, is a chain-type stitch and incrementally releasable by traction on the release string 32 slidably engaged through the first delivery catheter 38 to allow release of the sheath 30 or other releasable restraint, in two segments 33a and 33b, for a staged deployment of the device 10 from its collapsed position in FIG. 2a.

As depicted in FIGS. 1 and 2a, in one preferred mode of the device 10, the restraint would provide for two separately releasable component sections 33a and 33b in a sequential releasable restraint of the bifurcated prostheses 12 which allows for sequential expansion of the first component 19 (comprising the trunk 14 and cuff 22), and subsequently the ipsilateral leg 18 in sequential steps and at appropriate times chosen by the surgeon. The second leg 28 shown in the FIG. 10, is engaged to a second delivery catheter 34 in a collapsed state for translatable delivery along a positioned guide wire 55 to an engagement with the expanded cuff 22. The leading end 29 of the contralateral or second leg 28 shown in FIG. 10, is adapted to cooperatively engage with the distal end 24 of the expanded cuff 22.

The first delivery catheter 38 is advanced through an axial passage running through the interior of the first leg 18 over a first guide wire 35. As shown in FIGS. 1 and 2a, the escort catheter 40 is slidably engaged with the first delivery catheter 38 and with its distal end projecting from an exit aperture 41 in the first delivery catheter 38 as depicted in FIGS. 1 and 2a. In this configuration the distal end of the escort catheter 40 is covered in an engagement under the first release component 33a to maintain the escort catheter 40 streamlined and adjacent to the delivery catheter 38 during initial deployment (FIG. 2a).

A second guide wire 36 projects from the distal end of the escort catheter 40 and is pre-positioned within the cuff 22 prior to compression of the first component 19 to the collapsed state in which it is held by the releasable component sections 33a and 33b depicted in FIG. 1, or other means of sequentially releasable restraint. As shown in FIG. 2b this distal end engagement may be accomplished by passage of the tip of the escort catheter 40 through the release stitch 31 thereby allowing for easy sequential release by the surgeon of the first component section 33a along with the escort catheter 40. The second guide wire 36 thus remains pre-positioned in the cuff 22 for subsequent employment as a guide into the cuff 22 once the first releasable component 33a is released expanding the trunk 14 and cuff 22.

Figure 2:
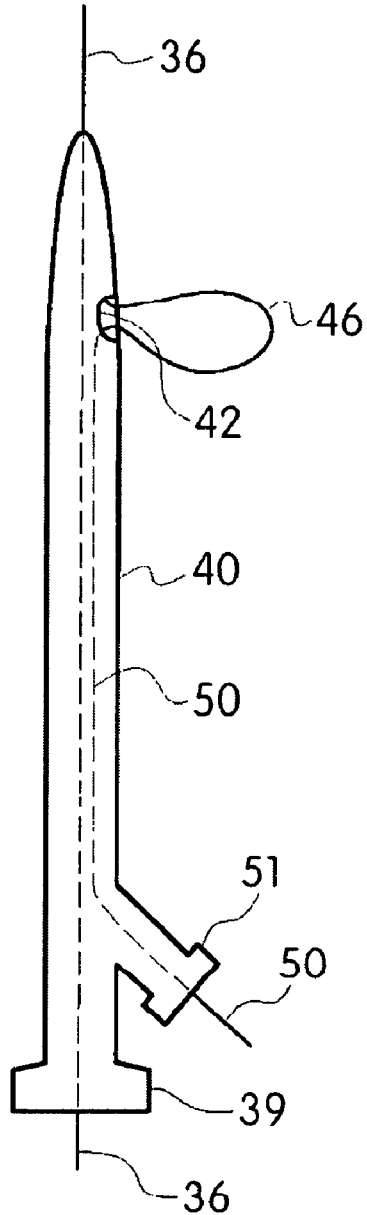
FIG. 2 depicts the escort catheter and an extending snare and control wires.
Figure 2A:
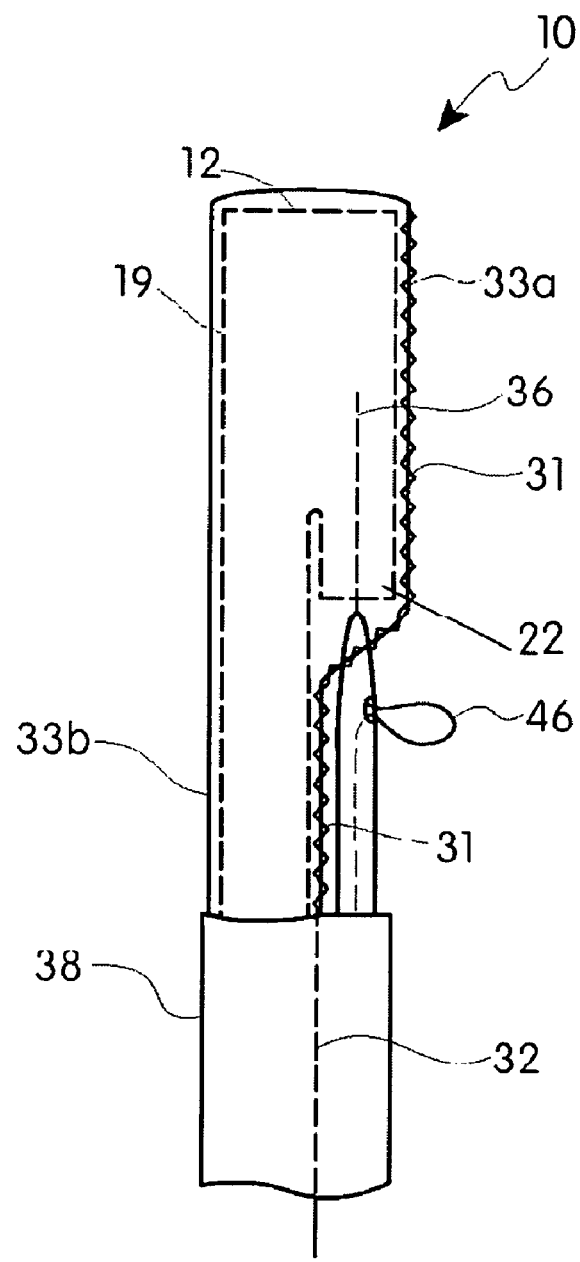
FIG. 2a depicts the device incorporated into the delivery catheter and a release stitch providing a two-stage release of a restraint during deployment.
Figure 2B:
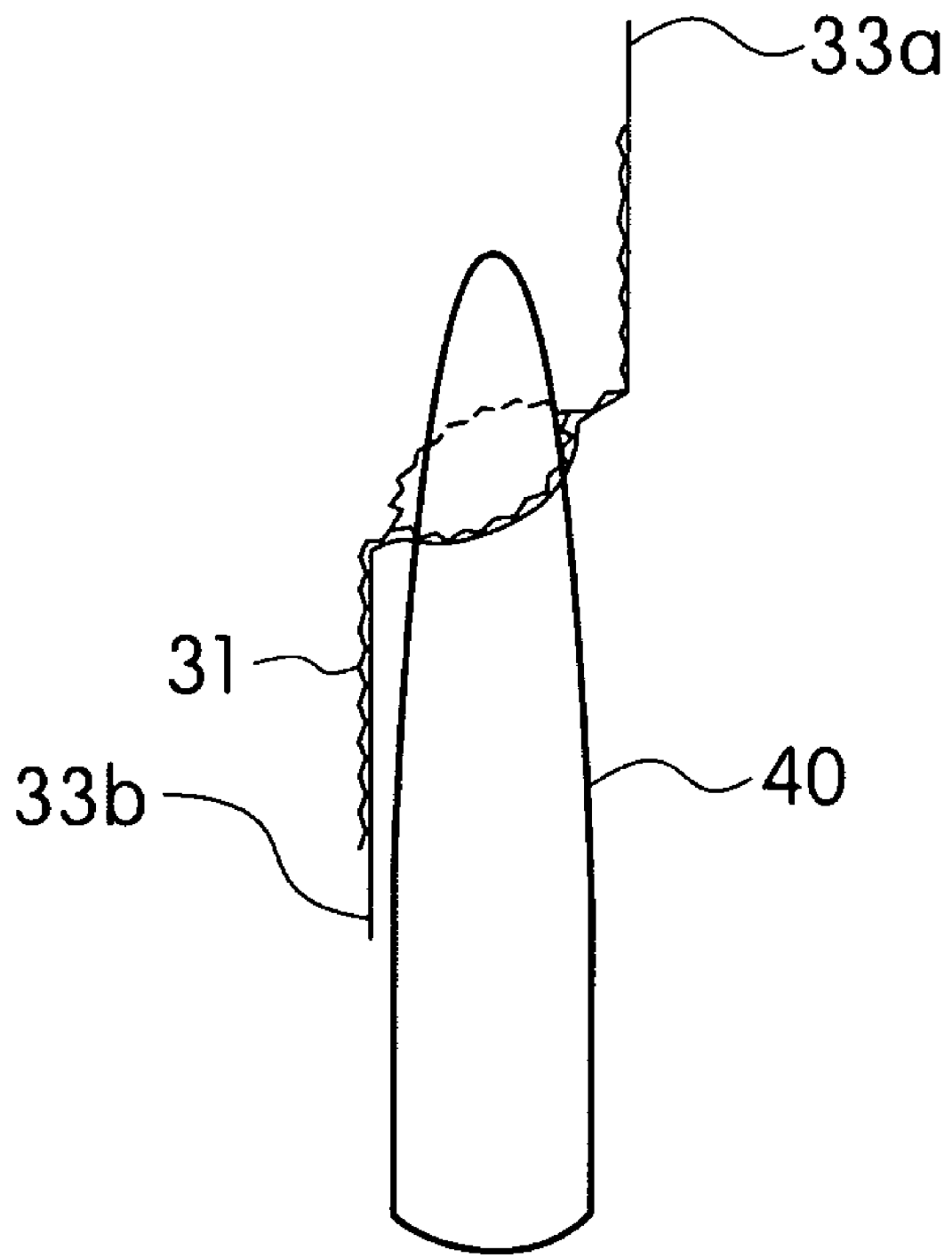
FIG. 2b shows a close up of the escort catheter and the engagement of the distal end of the escort catheter through the release stitch and under the first of two release components engaged around the bifurcated prostheses.
Figure 3:
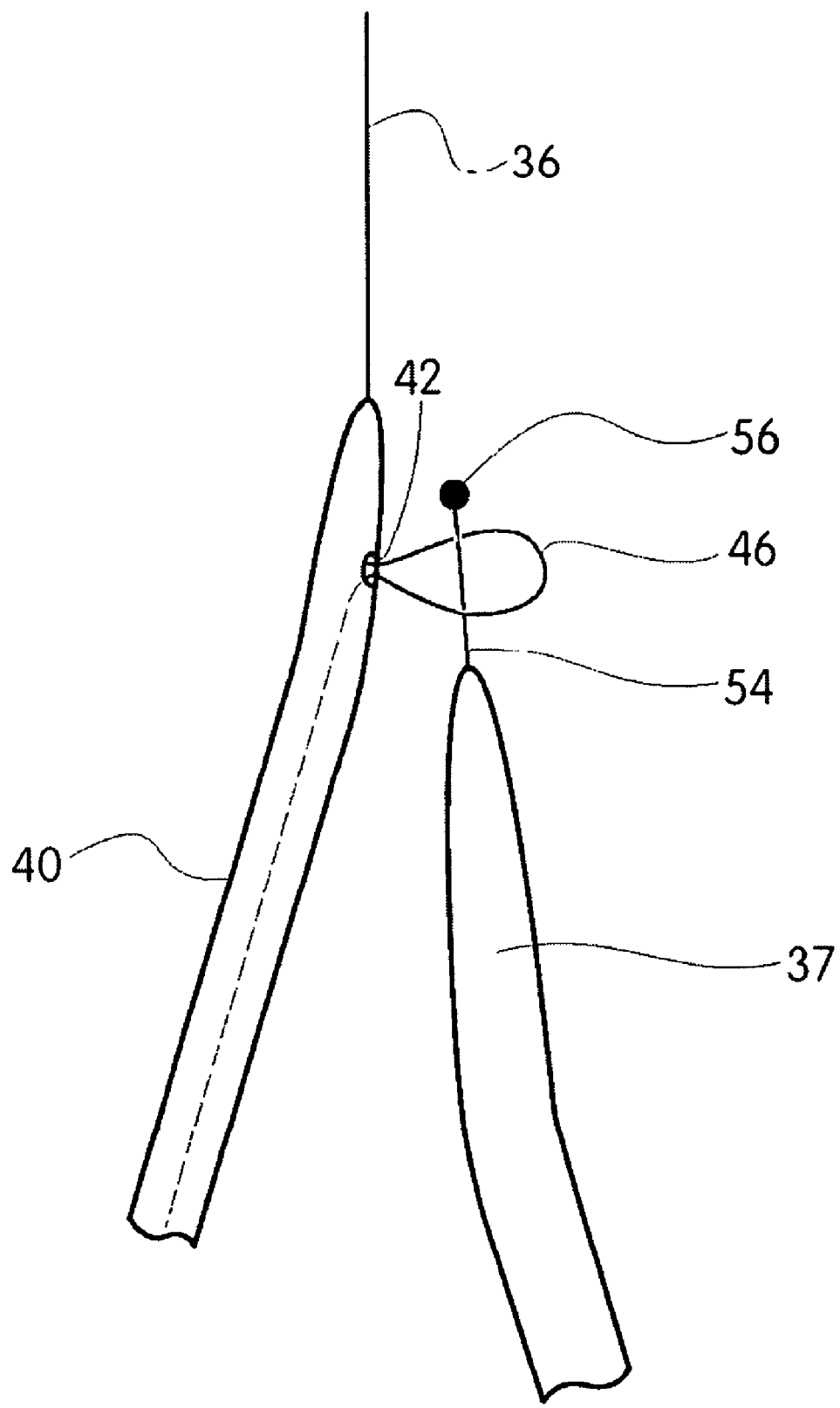
FIG. 3 depicts the capture of a third guide wire using a snare extendable from the escort catheter.

In a preferred mode of the device 10 shown in various views in FIGS. 1-3, communicating from an exit aperture 42 in the escort catheter 40, is a wire capturing means shown as a snare 46 in FIG. 2a. The snare 46 is preferably formed of memory material such as nitinol to a predetermined preferred deployed shape and controllable size by the operator. A snare control wire 50, or other means for cinching and expanding the projecting snare 46, is translatably engaged axially through the escort catheter 40 and through a locking valve 51 positioned exterior to the body of the patient. The snare 46 can thus be extended to a loop of a desired size or collapsed by translation of the control wire 50 and held in that position by the locking valve 51.

Figure 8:
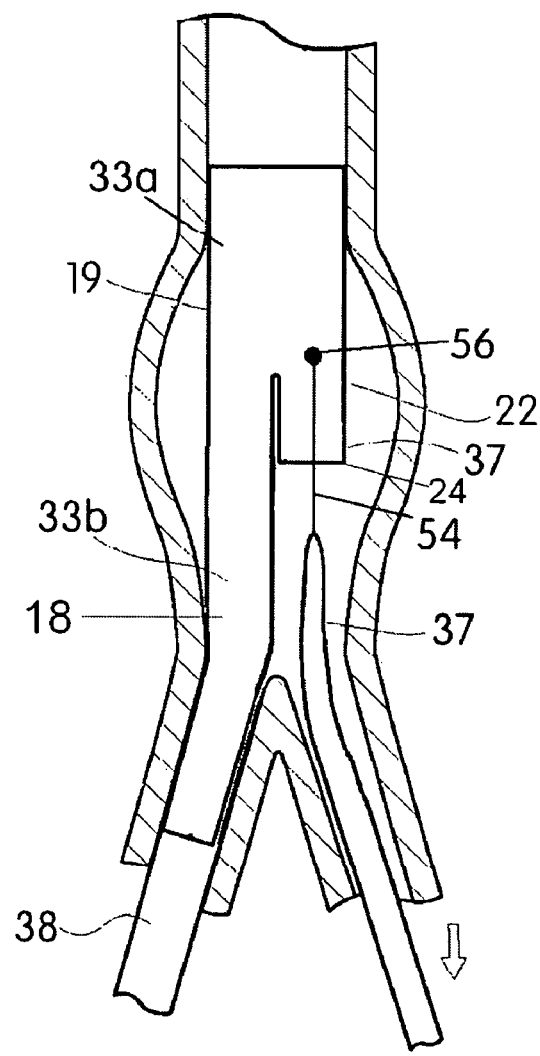
FIG. 8 shows the third guide wire positioned in the cuff after release of the snare and removal of the escort catheter.

During implantation, the first component 19 shown expanded in FIG. 8, formed of the trunk 14, first leg 18, and cuff 22, and shown in FIG. 1 in a collapsed position on the distal end of the first delivery catheter 38, is translated over the pre-positioned first guide wire 35 (FIG. 1), through a femoral artery. The first component 19 in the collapsed position is advanced to a position within the aorta so that the aperture 42 of the escort catheter is adjacent to the juncture of the second iliac artery and the aorta.

Prior to the sequential release of the compressed first component 19, and once the surgeon has determined proper placement in the aorta, the snare 46 is deployed from the exit aperture 42 in the escort catheter 40, to form a loop by employment of the snare control wire 50. The loop of the snare 46 as noted, is properly positioned by the surgeon at the juncture of the second iliac artery and the aorta. Means for positioning of the snare 46 is provided by one or a combination of extensions of the snare 46, translation of the delivery catheter 38 and rotation of the delivery catheter 38, to thereby properly deploy the snare 46 extending from the escort catheter 40 in a position for a capture of a third guide wire 54 inserted from the contralateral femoral artery as depicted in FIG. 4.

Figure 4:
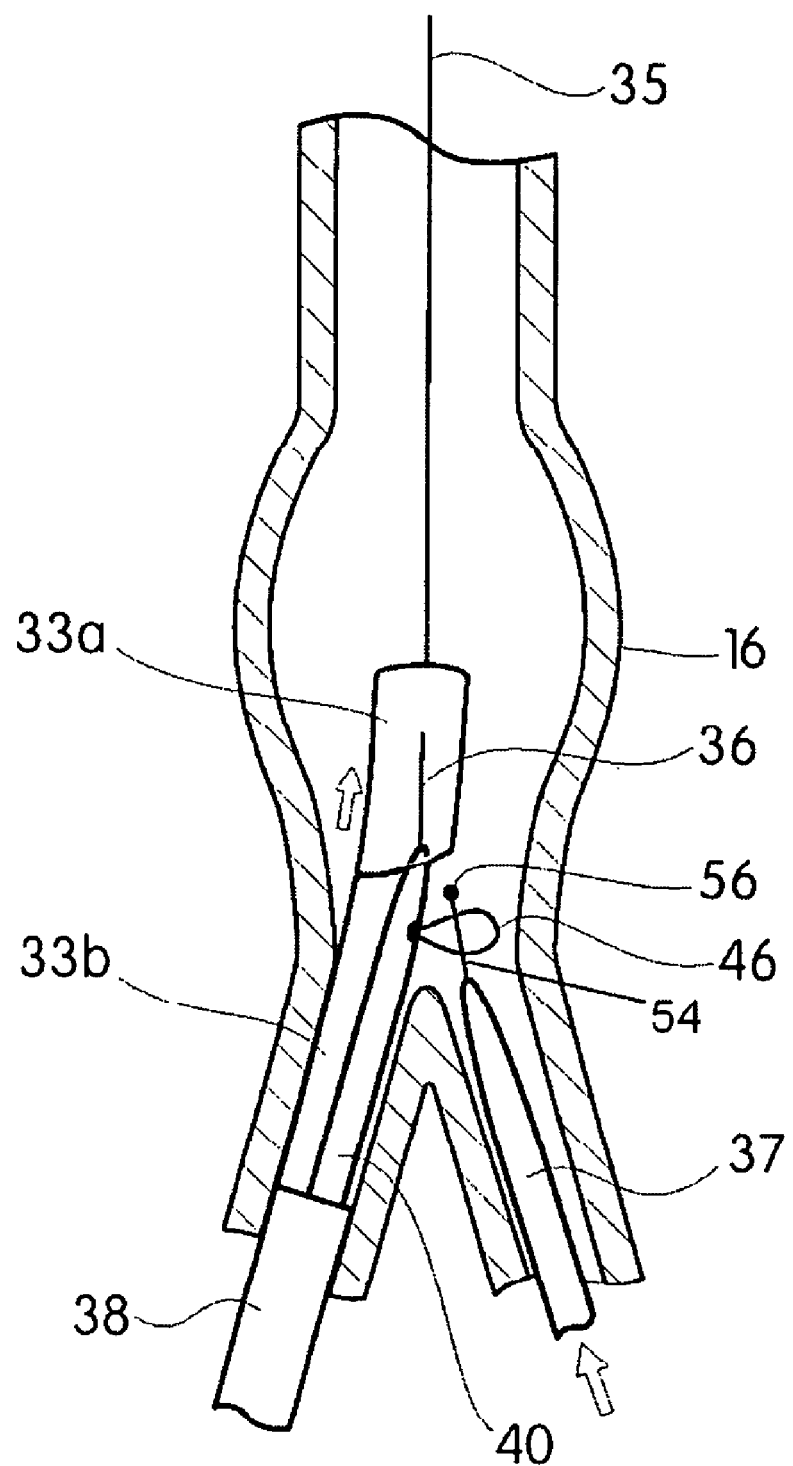
FIG. 4 shows insertion of the delivery catheter to a position at the juncture of the second iliac artery and the aorta and deployment of the snare capture device from the escort catheter.

Upon proper positioning of the first component 19, and the snare 46, a guide catheter 37, having the third guide wire 54 extending from its distal end, is translated through the opposite leg artery shown in FIG. 4. As noted, in a preferred mode of the device 10, the third guide wire 54 is extendable from the distal end of the guide catheter 37 and has a bead 56 or similar means for maintaining a secure capture within the cinched snare 46. Other means to maintain the snare 46 on the third guide wire 54 may be employed as would occur to those skilled in the art and such are anticipated. The main object being that the snare 46 maintains its engagement to the third guide wire 54 during manipulation of the device 10 after the capture, to a desired positioning within the aneurysm. This secured engagement of the cinched snare 46 and escort catheter with the captured third guide wire 54, allows for subsequent translation of the escort catheter 40 along the second guide wire 36, and concurrent translation of the captured third guide wire 54 into the cuff 22 without risk of a detachment therefrom.

As shown in FIG. 4, in the positioning step, the distal end of the third guide wire 54 and the guide catheter 37 are translated to a point wherein the bead 56 passes through the pre-positioned and extended snare 46. Once so positioned, the snare control wire 50 is translated to close the loop and capture the distal end of the third guide wire 54. This cinched snare 46 around the third guide wire 54 behind the bead 56 thereby provides means for positive mechanical engagement of the escort catheter 40 to the third guide wire 54. A locking valve 51 is then set to maintain the snare 46 cinched. As noted, once so captured, the delivery catheter 38 may be manipulated by the surgeon for proper position for deployment of the first component 19 in the aneurysm, as depicted in FIGS. 5-6. During this positioning, capture of the third guide wire 54 is maintained, whether the delivery catheter 38 is translated or rotated.

Figure 7:
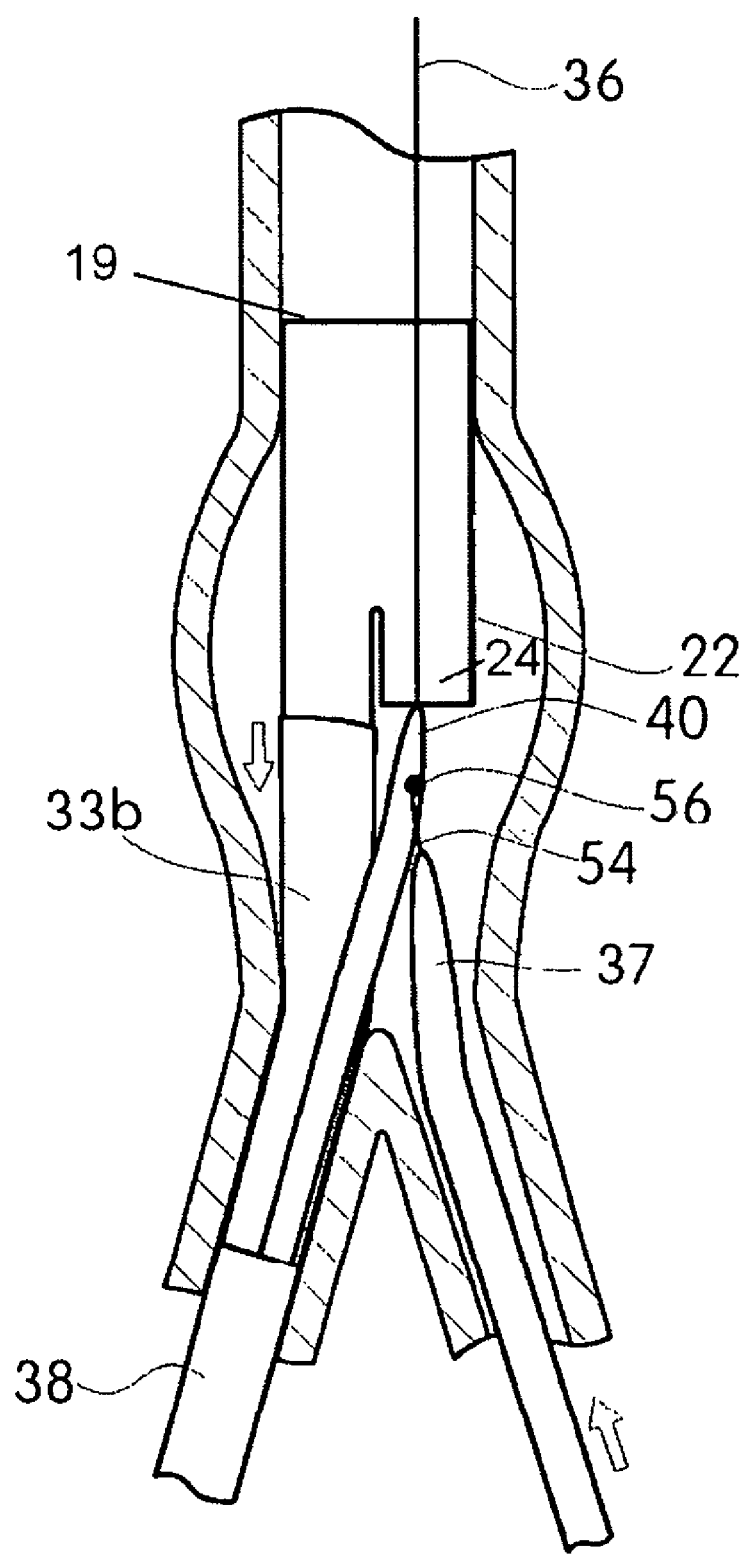
FIG. 7 depicts translation of the escort catheter and captured third guide wire into the expanded cuff.
Figure 7A:
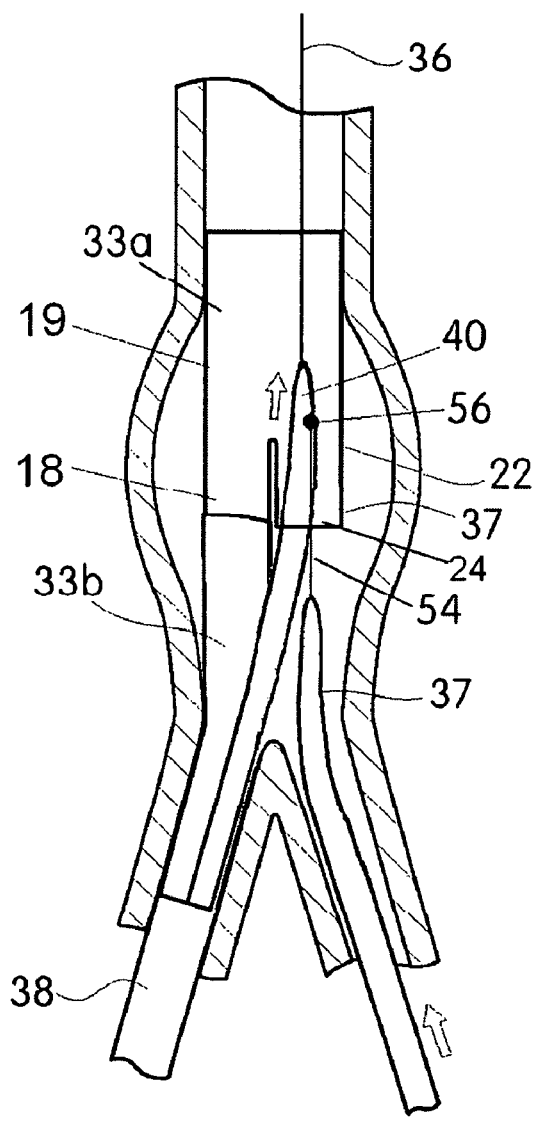
FIG. 7a shows the escort catheter and third guide wire fully translated into the expanded cuff ready for release from its engagement with the snare.

Once the first component 19 is properly positioned, the first releasable portion 33a of the restraining device shown as the sheath 30, is released as shown in FIGS. 6-7. Release as noted is in two stages through the disengagement of the release stitch 31 by translation of the release string 32 (FIG. 2a). Release of the first releasable portion 33a expands the trunk 14 and the cuff 22 in the aorta and also releases the distal end of the escort catheter 40 from its engagement under the first releasable portion 33a of the fabric sheath 30. The first leg 18 portion in the preferred mode of the device remains compressed within the second releasable component 33b for subsequent deployment.

With the third guide wire 54 captured against the side of the escort catheter 40, the escort catheter 40 is now translated along the pre-positioned second guide wire 36 extending into the now expanded cuff 22 as depicted in FIG. 7. This translation of the escort catheter 40 moves the snare-engaged third guide wire 54 into the interior of the cuff 22 easily, thereby eliminating a time-consuming, costly, radiation-intensive and frustrating component in current versions of the procedure.

Once the surgeon ensures passage of the third guide wire 54 into the cuff 22, the snare 46 may be released and the second guide wire 36 and the escort catheter 40 removed. The third guide wire 54 is maintained in position inside the cuff 22 while the escort catheter 40 and snare 46 are removed. With the third guide wire 54 in position, the second releasable portion 33b may be released to deploy the ipsilateral or first leg 18 of the graft in place in the artery. Release of the second releasable portion 33b is accomplished by finishing the unwinding of the release stitch 31 through a translation of the release string 32. Thereafter the first delivery catheter 38 is removed leaving the first component 19 engaged in place in the aorta as shown in FIG. 8.

With the first component 19 so engaged, as will be evident to those skilled in the art, employing the properly positioned third guide wire 54 as a guide any of a number of conventional wire exchanges may be executed by the surgeon using the third guide wire 54 to properly position subsequent sheaths or guide wires having their distal ends easily positioned inside the cuff 22. For instance, the surgeon may advance a wide lumen sheath over the third guide wire 54 to a position with its distal end inside the cuff 22, whereafter the third guide wire 54 may be removed through the wide lumen axial cavity of the sheath. Thereafter a wire 55, of the surgeon's choice, as shown in FIG. 9, may be properly positioned through the axial cavity to place its distal end inside the cuff 22.

Using the wire exchange and the subsequently placed wire 55, the surgeon then advances a secondary delivery catheter 34 thereover to properly position the second component of the bifurcated stent graft 12, which is the contralateral or second leg 28. Such a proper positioning with the leading end 29 of the collapsed second leg 28 within the distal end 24 of the cuff 22 is easily accomplished translating the second delivery catheter 34 over the wire 55. So positioned, the second leg 28 is then deployed by activating a secondary release string 58 to release the means for constraint of the second leg 28 from its collapsed position as depicted in FIG. 9 to an engagement with the cuff 22 as depicted in FIG. 10.

Figure 11:
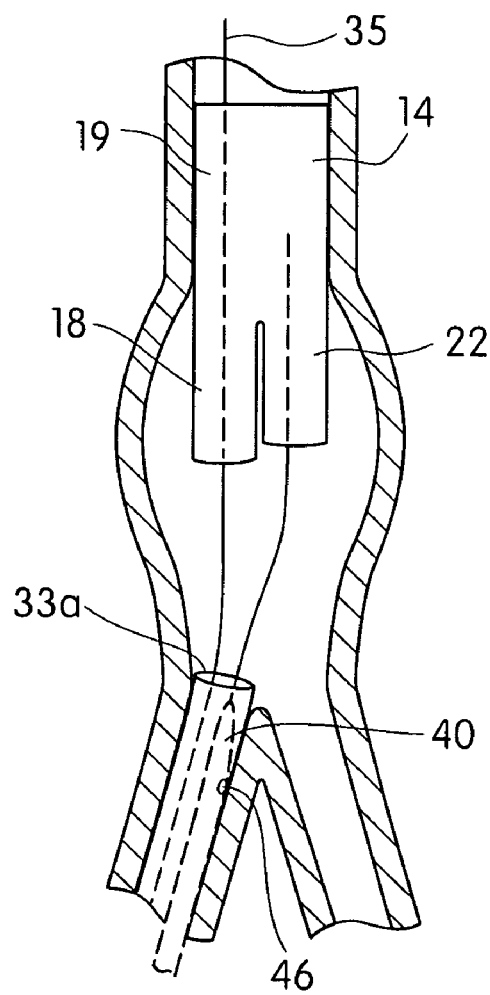
FIG. 11 depicts another preferred embodiment of the device and method herein wherein a conventionally employed sheath delivery system is used for implantation showing the escort catheter translatably engaged therein.

Another preferred mode of the device is depicted in the view of FIG. 11 which operates essentially the same as the above noted embodiment. This mode of the device is employed with conventional implant delivery systems which employ a cylindrical sheath 33a with engageable components such as those by the Cook Group of Bloomington, Ind. Such systems conventionally employ the sheath 33a as a conduit for the collapsed bifurcated stent graft 12 using a push wire to translate and deploy the stent graft 12 from the distal end of the sheath 43. As those skilled in the art will readily discern, many types of delivery systems and means to constrain such stent grafts 12 to their collapsed state and translate them to proper placement are employable using the device 10 and method herein since the device 10 and method are not dependant on the constraint type, nor the conduit, sheath, or catheter.

Figure 12:
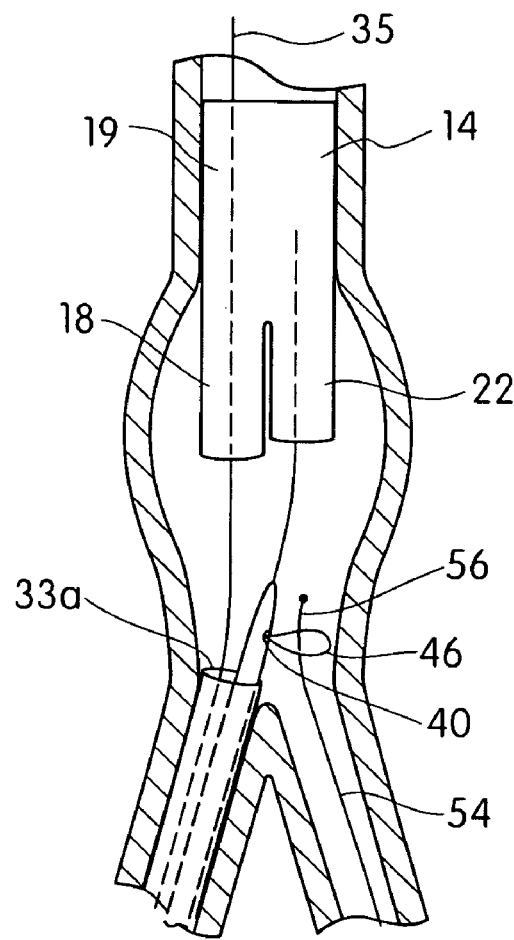
FIG. 12 depicts the device shown in FIG. 11 wherein the escort catheter has been extended from the distal end of the sheath delivery system and the snare deployed for a capture.

As depicted in FIGS. 11-12, second guide wire 36 is pre-positioned in the cuff 22 and provides the means to guide a preengaged capture component such as the snare 46 or basket 47 (FIG. 13) into the cuff 22. Translation of the capture component such as the snare 46 or basket 47 into the cuff 22, along the second guide wire 36, once the capture component engages the supplemental guide means such as the depicted third guide wire 54, thus results in easy and quick placement of the pictured captured third guide wire 54, or other supplemental guide means as would occur to those skilled in the art, into the cuff 22. Once the third guide wire 54 or other supplemental means is guided into the cuff 22, it provides a defined path for the subsequent communication and engagement of contralateral or second leg 28 with the cuff 22 or intermediary guides therefor.

As noted, in FIG. 11 a conventionally employed sheath 33a delivery system is shown with the escort catheter 40 translatably engaged therein.

Upon delivery of the first component 19, as shown in FIG. 12 the escort catheter 40 may be extended from the distal end of the sheath 43. Thereafter the snare 46, basket 47, or other capture component may be deployed for a capture of the third guide wire 54 or other translatable guide means which is then positioned to provide a pathway for the contralateral or second leg 28 into an engagement with the cuff 22. Once the snare 46, basket 47 or other capture component is engaged to the third guide wire 54 or other guide means, they may ride along the second guide wire 36 thereby taking the third guide wire 54 or other captured guide means into the cuff 22 or aperture where the second guide wire 36 was originally pre-positioned.

Figure 13:
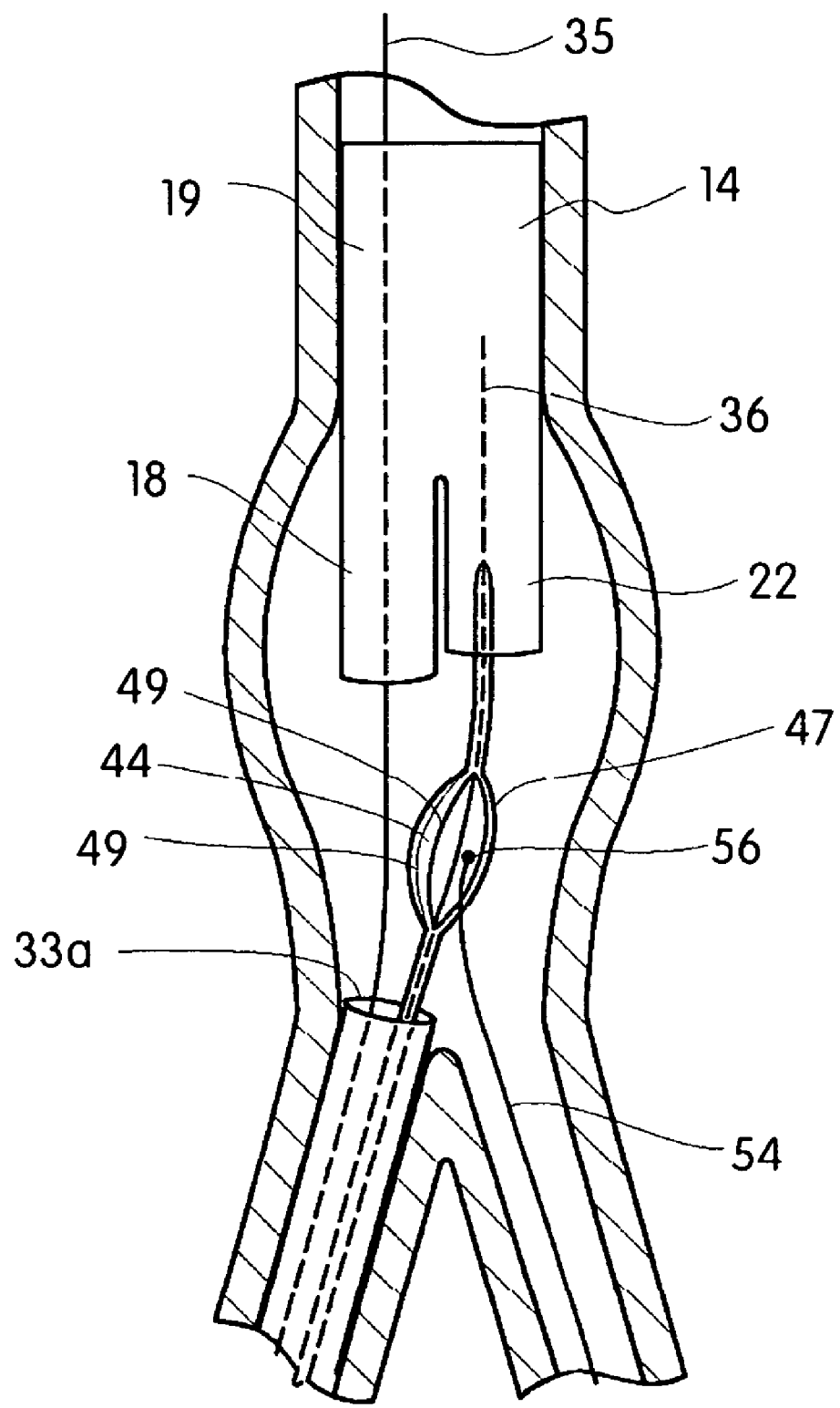
FIG. 13 shows another mode of an escort catheter or translatable capture component wherein a collapsible basket provides the means to mechanically capture the third guide wire or other means providing a rail or guide to the leg to be engaged.

As depicted in FIG. 13, and noted earlier, the snare 46 (FIG. 12) may be substituted by another controllable capture component such as the depicted basket 47. The basket 47 employs a plurality of radially deployed wires 49 to form gaps 44 therebetween to capture of the third guide wire 54 when a control contracts the plurality of wires 49 to close the gaps 44. Subsequent to this capture, the basket 47 rides the pre-positioned second guide wire 36 into the cuff 22 pulling the third guide wire 54 or other guide means for the contralateral leg to follow to its engagement with the cuff 22.

As depicted in FIGS. 14 and 15 other modes of the device may be employed a capture component such as a snare 46 which is operationally engaged to ride along the second guide wire 36 or may reside parallel to the guide wire 36 (FIG. 15). While the snare 46 is noted as especially favored for its compactness and angled deployment, those skilled in the art once exposed to this application will no doubt design other capture components to engage a pre-positioned guide and all such alternatives are envisioned within the scope of this application.

In FIGS. 14 & 15, the snare 46 type capture component projects from the distal end of the same lumen which houses the second guide wire 36. This lumen shown as a sheath 43 functions similarly to the escort catheter 40 already described above, but employing a snare 46 deployment at a distal end instead of from a side aperture. In such a deployment from the sheath 43, the snare 46 may be either slidably engaged to the second guide wire 36 as in FIG. 14, or tethered at a point 57 adjacent to the rim of the open end of the sheath 43. As noted, the snare 46 is formed of memory material and can be made to project sideways away from the long axis of the sheath 43.

The sheath 43 may be formed of a very low profile, substantially the diameter of a conventional angiographic guide wire of approximately 0.035 inches. The sheath 43 may slide relative to the pre-positioned guide means provided by the second guide wire 36 as shown in FIGS. 15*a* and 15*b* and/or relative to both the second guide wire 36 and a snare control wire 50 of a small caliber such as for example substantially 0.014 inches.

In these modes of the device the capture device formed by the sheath 43 and axially disposed second guide wire 36 and snare and control wire 50 (FIG. 14), will have an extremely low profile and easily incorporated into conventional delivery systems for stent graft devices. The snare 46 size can be regulated by advancing or retracting the control wire 50 axially engaged in the sheath 43, which may be engaged to the snare 46, or may be part of a unitary snare 46 and wire component.

A stop 39 is incorporated upon the second guide wire 36 of the mode of the device depicted in FIG. 14. This stop 39 constrains the sliding motion of the snare 46 if slidably engaged thereon, thereby enabling its proper function.

As noted, FIGS. 16-20 depict another preferred mode of disclosed device 10 which pre-positions a guide member 59 in the cuff 22 and thereby provides the means to guide a capture component such as the snare 46 or basket 47 (FIG. 13) into the cuff 22. In this mode of the device 10, the function of the second guide wire 36 is provided by a second guide member 59 which is a fixed extension from the distal end of the escort catheter 40. Consequently, in operating as a pre-positioned guide into the cuff 22, the guide member 59 does so by leading the escort catheter 40 into the cuff 22 rather than acting as a rail for translation of the escort catheter 40.

Figure 16:
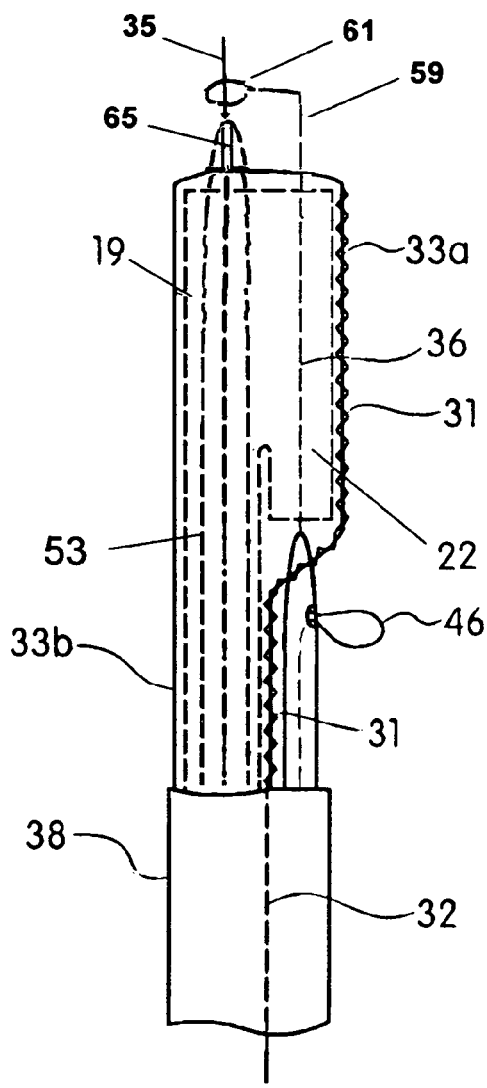
FIG. 16 depicts a mode of disclosed device having a fixed extension projecting from the end of the escort catheter adapted at its other end to slidably contact with the distal end of the core shaft of a delivery catheter, slidably engaged with a guide wire over which the device is introduced into the body of a patient.
Figure 17:
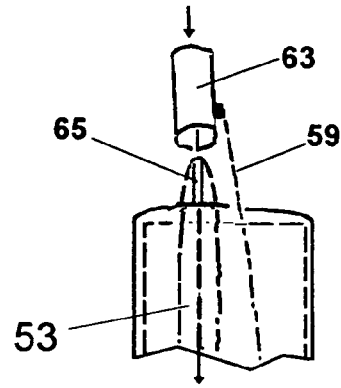
FIG. 17 shows the distal end of the fixed extension employing a tube for a contact with core shaft and slidable engagement with the guide wire.
Figure 19:
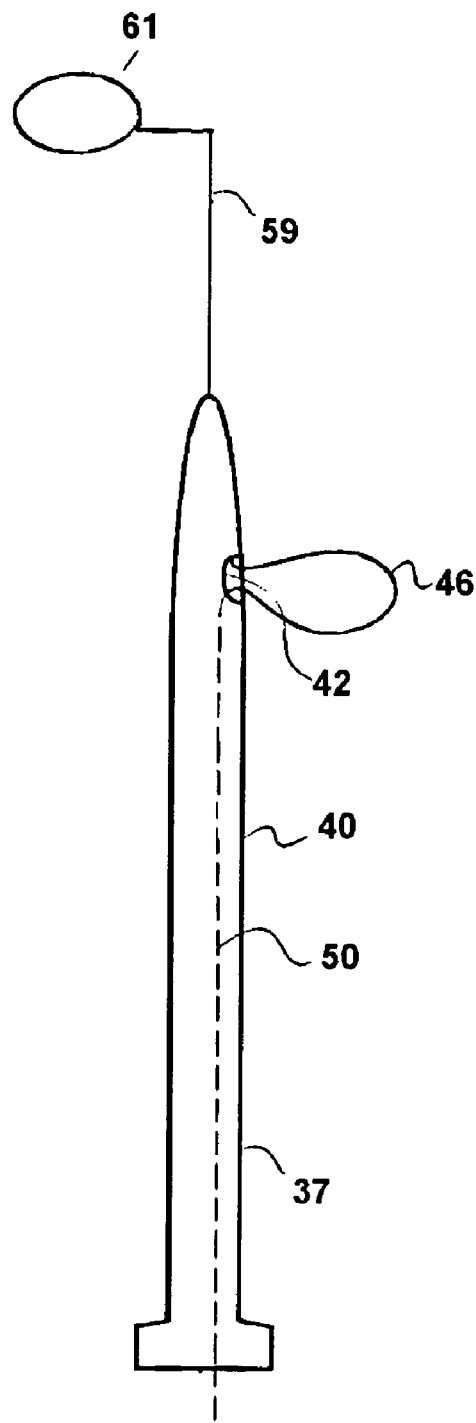
FIG. 19 shows one preferred mode of the escort catheter having a loop engaged from the distal end of a fixed extension with the loop spaced from the axis of the escort catheter.
Figure 20:
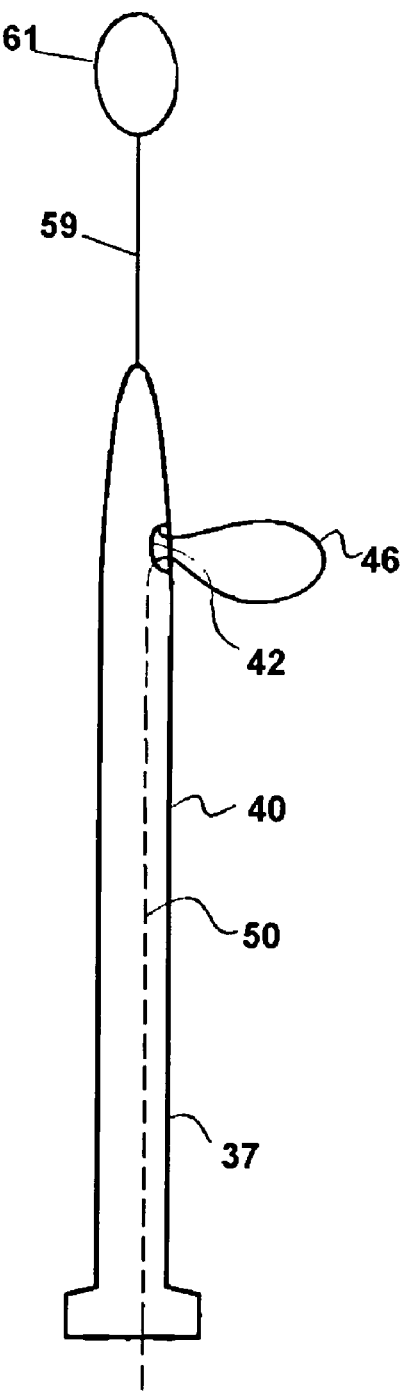
FIG. 20 depicts another preferred mode of the escort catheter having the loop or other means for contact with the distal end of the core shaft positioned at the distal end of the flexible fixed extension.

As shown in FIG. 16, the device 10 in a collapsed state has the guide member 59 extending through the cuff 22 and projecting from the opposite side of the first component 19. At the distal end of the guide member 59 is positioned a means for translatable contact with the distal end of the core shaft 53 which itself is translatably engaged through the delivery catheter 38 and which has an axial passage 65 over which the graft is introduced into the patient along the guide wire 35. As shown in FIGS. 16, 19, and 20 this means for translatable contact with the distal end of the core shaft 53 is a loop 61 which concurrently engages around the guide wire 35. In FIG. 17, the cylinder 63 is provided in place of the loop 61 and is also adapted to contact the distal end of the core shaft 53 as well as to encircle the guide wire 35 such that translation of the core shaft 53 in contact with the cylinder 63 will slide the guide member 59 along upon its engagement to the guide wire 35.

As those skilled in the art will realize, the dimensional characteristics of any employed means for translatable contact of the distal end of the core shaft 53 with the guide member 59 will be dependent on the shape of the core shaft 53. Consequently all such contact means as would occur to those skilled in the art, to slide the guide member 59 with the core shaft 53 are anticipated. Encirclement of the guide wire 35 over which the core shaft 53 rides, may also be adapted by those skilled in the art and is anticipated within the scope of this invention.

In operation of the device 10 once the first guide wire 35 is inserted into the patient and positioned properly in a conventional fashion, the axial passage 65 of the core shaft 53, which is translatably engaged through the delivery catheter 38, is engaged upon the first guide wire 35. During this engagement step, the first guide wire 35 is also threaded through the loop 61 or cylinder 63 or other means of slidable engagement extending from the device 10 in its compressed state, and then into the axial passage 65. Thereafter the delivery catheter 38 is translated to its proper position in the patient for deployment of the device 10. The core shaft 53, may also be translated independently of the delivery catheter 38, over the guide wire 35.

Figure 18:
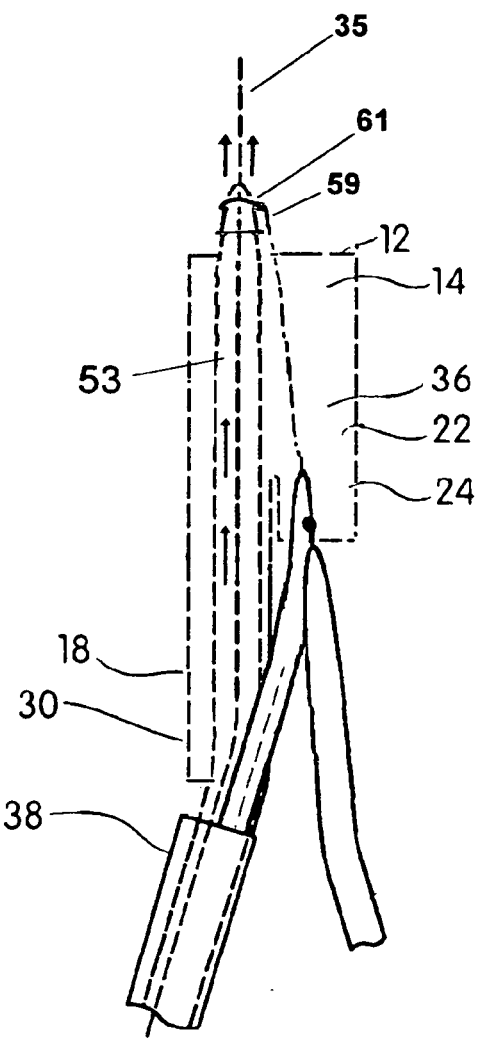
FIG. 18 depicts translation of the escort catheter using a translation of the guide-wire engaged core shaft to pull the escort catheter into the cuff.

Deployment is accomplished substantially the same as noted above as is capture of the third guide wire 54 by the snare 46. As shown in FIG. 18, once the third guide wire 54 is so captured, or other means to guide the second component as the case may be, the core shaft 53, with the loop 61 or cylinder 63 positioned thereon, may be translated past the first component 19 and into the blood vessel. This translation with the loop 61 or cylinder 63 in contact with the distal end of the core shaft 53, thereby exerts a force upon the second guide member 59 pulling it and the previously engaged escort catheter 40, into the cuff 24. This mode of the device 10 allows the escort catheter 40 to be securely anchored in the cuff 24 by virtue of the engagement of the guide member 59 to the guide wire 35.

In subsequent operation, once the third guide wire 54 is positioned in the cuff 24, the device 10 is employed in the same fashion as the mode of the device 10 which translates the escort catheter 40 along the second guide wire. The second guide member 59 need not be metal but needs only to be sufficiently strong to bear the force of pulling the escort catheter 40 when pulled itself by the translation of the translating core shaft 53. The engagement to the distal end of the escort catheter 40 must also be sufficiently strong to bear the load of pulling the escort catheter 40 by the translation of the core shaft 53.

In yet another mode of operation, after the capture of the third guide wire by the snare 46, the escort catheter 40 may also be advanced into the cuff 24 by translating the escort catheter 40. Since the distal end of the guide member 59 is securely engaged to the guide wire 35, and the proximal end of the guide member 59 is engaged with the escort catheter 40, translation of the escort catheter 40 will slide the guide member 59 in its engagement to the guide wire 35. The captured third guide wire 54 may thus be carried into the cuff 24 by the pre-positioned guide member 59 riding its engagement to the guide wire 35 when the escort catheter 40 is pushed or translated toward the cuff 24.

Alternatively, one or a combination of a translation of the escort catheter 40 by pushing upon it with the guide member 59 engaged to the guide wire 35, and a translation of the core shaft 53 which is adapted to contact with and push distal end of the guide member 59, may be employed to properly position the pre-captured third guide wire 54 into the cuff. This option provided by the distal end of the guide member 59 being engaged to the guide wire 35 and adapted for slidable contact with the core shaft 53 which is slidably engaged on the guide wire, provides the surgeon increased utility during engagement and assembly of the device 10 in the patient.

As has been noted above, upon being educated by this disclosure, it is anticipated that those skilled in the art will no doubt realize that the device 10 and method herein, may be adapted to aid in the internal assembly of many types of modular or assembled endoprosthesis which require assembly of one or more components during an implantation to form a fluid conduit. As such, the use of the terms cuff 22 and stent graft 12 herein are intended to include any implantable device where a first component is deployed in a blood vessel or other organ of a patient, which must be subsequently engaged to a one or more subsequent components to form fluid or other conduits with the assembled implant.

The disclosed system of pre-positioning of a guide means within the intended aperture or conduit of a first component, to provide a path or raceway for an engaged capture component, and adapting that capture component to removably engage a secondary guide means for a subsequently engaged prosthesis component, is easily adapted by those skilled in the art to any number of assembled endoprosthesis. By pre-positioning a first guide means such as second guide wire 36, or guide member 59, prior to constraining of the first component of the prosthesis, thereby positioning that first guide means within the intended engagement passage for a subsequent component, when the first component of the prostheses is deployed, a capture component, engaged upon the first guide means, may quickly translate any captured secondary guiding component along the first guide means and into the engagement passage. The subsequent positioning of the second component of the prosthesis to the first, along that secondary guiding component or a subsequently placed guide using the secondary guiding component, renders assembly of the implantable device much safer as well as easier and faster in all instances.

Consequently those skilled in the art, will no doubt adapt this pre-positioning of a first guide means engaged to a capturing component, for a proper positioning of a second guiding component to many other implantable devices. All such adaptations or modifications as would occur to those skilled in the art are as such anticipated within the scope of this application.

Further, the method and components shown in the drawings and described in detail herein disclose arrangements of elements of particular construction and configuration for illustrating preferred embodiments of structure and steps for deployment of the present invention. It is to be understood, however, that elements of different construction and configuration than those depicted and describe, and using different steps and process procedures, and other arrangements thereof, may be employed for providing for the guiding of a second prostheses component to an engagement with the first prosthesis component in accordance with the spirit of this invention.

As such, while the present invention has been described herein with reference to particular embodiments thereof, a latitude of modifications, various changes and substitutions are intended in the foregoing disclosures, it will be appreciated that in some instance some features of the invention could be employed without a corresponding use of other features without departing from the scope of the invention as set forth in the following claims. All such changes, alternations and modifications as would occur to those skilled in the art are considered to be within the scope of this invention as broadly defined in the appended claims.

Further, the purpose of the abstract of the invention, is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting, as to the scope of the invention in any way.

What is claimed is:

1. A stent graft assembly formed of a first component in an engaged position with a second component to define a fluid conduit through the engaged components, comprising:

said first component having a trunk portion defined by a body wall surrounding a central passage which communicates at a first end with a first aperture in said body wall and having a second end, opposite said first end;

at least one secondary aperture communicating through said body wall with an axial passage communicating between said secondary aperture and said central passage;

said second component having an axial passageway communicating between a first end and a distal end;

said first end of said second component engageable with said secondary aperture;

said first component having a compressed state and an expanded state;

an elongated guide, said guide having an engaged position with said guide communicating through said axial passage and said central passage from a first end extending from said secondary aperture to a second end projecting from said first aperture of said first component in said compressed state;

means for a slidable engagement of said second end of said elongated guide in said engaged position, upon a guide wire communicated from said first end through said central passage and exiting said first component at said first aperture, and positioned in a blood vessel of a patent;

means for restraint of said first component in said compressed state with said elongated guide in said engaged position;

means for translation of said first component in said compressed state, along said guidewire, to an implantation position in a patient;

means to guide said second component to a position proximate to said implantation position;

means to capture said means to guide said second component in a releasable engagement, said means to capture said means to guide said second component engaged with said elongated guide;

said means to capture said means to guide said second component positionable to an inserted position communicating through said secondary aperture and positioned within said axial passage by a translation of said elongated guide along said guide wire; and said means to guide said second component, when in said inserted position, providing a means to guide said first end of said second component to said engaged position, whereby a fluid passage is formed by said central passage communicating through said axial passage with said axial passageway.

2. The stent graft assembly of claim 1 additionally comprising:

said means for translation of said first component being a first catheter having an axial passage communicating from a first end to a distal end;

said axial passage of said first catheter defining an axial conduit dimensioned for a translation over said guide wire;

said first component removably engaged at or adjacent to said distal end of said first catheter;

said means to capture said means to guide said second component is a second catheter, said second catheter having a first end, a second end, a snare adjacent to said second end, and having a control wire for cinching said snare; and said first end of said elongated guide engaged with said second end of said second catheter.

3. The stent graft assembly of claim 2 additionally comprising:

a core shaft translatably engaged within said axial passage of said first catheter;

said core shaft having a first end and having a second end projectable from said distal end of said first catheter by translation of said core shaft;

said core shaft having an axial channel communicating between said first end and said second end, said axial channel defining said axial conduit for said guide wire;

said second end of said elongated guide configured for a releasable engagement with said second end of said core shaft while in said slidable engagement with said guide wire; and translation of said core shaft while in said releasable engagement with said elongated guide, in a direction increasing said projection of said second end of said core shaft from said distal end of said first catheter, thereby inducing a translation of said elongated guide in a direction toward said first end of said first component and providing a means to pull said second catheter through said secondary aperture.

4. The stent graft assembly of claim 1 wherein said releasable engagement is a frictional or mechanical engagement of said means to guide said second component.

5. The stent graft assembly of claim 4 additionally comprising:

said means for translation of said first component being a first catheter having an axial passage communicating from a first end to a distal end;

said axial passage of said first catheter defining an axial conduit dimensioned for a translation over said guide wire;

said first component removably engaged at or adjacent to said distal end of said first catheter;

said means to capture said means to guide said second component is a second catheter, said second catheter having a first end, a second end, a snare adjacent to said second end, and having a control wire for cinching said snare; and said first end of said elongated guide engaged with said second end of said second catheter.

6. The stent graft assembly of claim 5 additionally comprising:

a core shaft translatably engaged within said axial passage of said first catheter;

said core shaft having a first end and having a second end projectable from said distal end of said first catheter by translation of said core shaft;

said core shaft having an axial channel communicating between said first end and said second end, said axial channel defining said axial conduit for said guide wire;

said second end of said elongated guide configured for a releasable engagement with said second end of said core shaft while in said slidable engagement with said guide wire; and translation of said core shaft while in said releasable engagement with said elongated guide, in a direction increasing said projection of said second end of said core shaft from said distal end of said first catheter, thereby inducing a translation of said elongated guide in a direction toward said first end of said first component and providing a means to pull said second catheter through said secondary aperture.

7. In a stent graft having a first component expandable from a collapsed state and removably engaged for delivery through a first blood vessel from a distal end of a first catheter traveling on a guide wire, and with said first component having a wall defining an axial passage communicating therethrough from a first end to a second end and having a secondary aperture communicating through said wall and in a communication with said axial passage, and which is adapted for an engagement with one end of an extension component having an axial passageway therethrough which is delivered through a second blood vessel, the improvement being:

a second catheter, said second catheter having a distal end exiting from or engaged to a position adjacent to said distal end of said first catheter, said distal end of said second catheter translatably positionable relative to said distal end of said first catheter;

a guide component, said guide component communicable through said second blood vessel;

means for temporary engagement of said guide component to said second catheter;

a guide member extending from the distal end of said second catheter and said guide member in an engaged position with said first component in said collapsed state, said guide member in said engaged position extending through said secondary aperture extending through said axial passage to a slidable engagement with said guide wire communicating through said axial passage of said first component, whereby subsequent to an expanding of said first component from said collapsed state, a translation of said second catheter with said guide member in said slidable engagement with said guide wire and with said guide component concurrently in said temporary engagement to said second catheter, provides means to position said guide component into said axial passage through said second aperture; and whereby said guide component so positioned in said axial passage, provides means to guide said one end of said extension component into said engagement with said secondary aperture.

8. The stent graft of claim 7 additionally comprising:
said guide component being a third guide wire translated through said second artery;
said means for temporary engagement of said guide component to said second catheter being a means to entrap said third guide wire into a captured state at a position adjacent to the distal end of said second catheter; and
translation of said second catheter with said guide member in said slidable engagement with said guide wire and said third guide wire in said temporary engagement to said second catheter, provides a pulling of said third guide wire through said second aperture and into said axial passage; and
wherein said third guide wire communicating through said second aperture and into said axial passage, provides a rail to guide said one end of said extension component, into said engagement with said second aperture.

9. A method for deploying a stent graft prosthesis formed of two engageable components in a blood vessel comprising the steps of:
(a) providing an expandable stent held in a collapsed state by a first restraining component, with said stent having a single axial passage at a first end communicating with both of a first passage extending to a first aperture and with a second aperture at a second end;
(b) providing a guide component positioned within said stent in said collapsed state and having a first end communicating through said axial passage and extending through said second aperture to an engagement with a translating member and having a second end extending from said axial passage at said first end of said stent;
(c) providing an expandable second component held in a collapsed state by a second restraining component, with said second component having an axial conduit therethrough which communicates with a first end which is engageable with said second aperture and;
(d) translating said collapsed stent along a guide wire running through said first aperture and said axial passage to a positioning of said collapsed stent in a blood vessel defined by a wall;
(e) releasing said first restraining component sufficiently to expand said stent into a contact point against said wall;
(f) employing a capturing component located on said translating member to engage a secondary guide for said second component;
(g) translating said guide component toward said first end of said stent to guide said translating member with said secondary guide engaged thereto, through said aperture and into said axial passage;
(h) releasing said capturing component to allow for a removal of said translating member;
(I) employing said secondary guide as a means to position said first end of said second component for an engagement with said aperture;
(j) releasing said secondary restraining component to allow for said engagement of said first end of said second component with said aperture.

10. The method for deploying a stent graft of claim 9 wherein said as a means to position said first end of said second component in said aperture comprises the steps of:
(k) employing said secondary guide extending from a position communicating through said second aperture, to a position outside the patient, as a rail to guide a sheath translated thereover into said axial passage through said second aperture;
(l) removing said secondary guide;
(m) translating a second guide wire through an axial passageway in said sheath and through said second aperture and into said axial passage;
(n) removing said sheath; and
(o) employing said second guide wire as a rail communicating though said axial conduit in said second component to translate said first end of said second component into position to engage with said second aperture; and
(p) releasing said secondary restraint.

11. The method for deploying a stent graft of claim 9 wherein positioning said collapsed stent in a blood vessel having a wall is accomplished by the steps of:
translating a distal end of a first guide wire into said blood vessel to a position adjacent to or past said point of contact;
engaging a proximal end of said guide wire through first passage and said axial passage and extending through said collapsed stent; and
pushing said collapsed stent engaged on said guide wire to a desired position in said blood vessel.

12. The method for deploying a stent graft of claim 11 with the additional step of:
engaging said proximal end of said guide wire through a slidable engagement at said first end of said guide component prior to engaging it through said first passage and said axial passage extending through said collapsed stent; and
allowing said first end of said guide component to slide on said guide wire when employing said guide component to guide said translating member and said secondary guide engaged thereto, through said aperture and into said axial passage.

13. A stent graft assembly formed of a first and second component which when engaged together define a fluid conduit through the engaged components, comprising:
said first component having a trunk portion defined by a body wall and an axial passage communicating at a first end with a first aperture in said body wall;
at least one secondary aperture communicating through said body wall to a secondary passage communicating with said axial passage;
said second component having an axial passageway communicating between a first end and a distal end;
said first end of said second component engageable with said secondary aperture to place said second component in an engaged position;
said first component having a compressed state and an expanded state and a restraint to maintain it in said compressed state;
a fluid passage communicating through said axial passage, said secondary passage and said axial passageway when said second component is placed in said engaged position;
an elongated guide having an engaged position extending from a first end inside said secondary passage through said secondary aperture to a second end projecting from said secondary aperture;
said first component in said compressed state with said elongated guide in said engaged position translatable to an implantation position in a blood vessel and engageable therein through a release or said restraint;

a secondary guide member communicable through a blood vessel, said secondary guide member having a leading end;

means to capture said leading end in a releasable frictional or a mechanical engagement;

said means to capture said leading end while in a said releasable engagement, translatable along a path defined by said elongated guide, to thereby position said leading end within said secondary passage; and said secondary guide wire with said leading end within said secondary passage providing a means to guide to said second component to said engaged position.

14. The stent graft assembly of claim 13 wherein:

said means to capture said leading end in a releasable frictional or a mechanical engagement is positioned proximal to the distal end of a catheter; and said elongated guide being a secondary wire extending though said catheter and exiting at said distal end thereof to extend through said secondary aperture to said first end positioned inside said secondary passage.

15. The stent graft assembly of claim 14 wherein said means to capture said leading end comprises:

a snare located adjacent to said distal end of said catheter; and a control wire to cinch said snare, communicating through an axial passage of said catheter.

16. The stent graft assembly of claim 15 wherein said catheter bearing said snare adjacent to said distal end, has a single lumen shared by said secondary wire and said control wire;

said snare projects from an aperture adjacent to said distal end of said catheter;

said distal end of said catheter narrows to an exit aperture located a tip of said distal end; and said exit aperture sized to accommodate only said secondary wire.

* * * * *